(12) United States Patent
Albert et al.

(10) Patent No.: US 7,403,110 B2
(45) Date of Patent: Jul. 22, 2008

(54) ENHANCED ALARM MONITORING USING A SOUND MONITORING SCREEN SAVER

(75) Inventors: David E. Albert, Oklahoma City, OK (US); Kathryn Marie Albert, Oklahoma City, OK (US)

(73) Assignee: Innovalarm Corporation, Oklahoma City, OK (US)

( * ) Notice: Subject to any disclaimer, the term of this patent is extended or adjusted under 35 U.S.C. 154(b) by 193 days.

(21) Appl. No.: 11/494,074

(22) Filed: Jul. 27, 2006

(65) Prior Publication Data

US 2006/0279418 A1 Dec. 14, 2006

Related U.S. Application Data

(62) Division of application No. 10/897,487, filed on Jul. 23, 2004, now Pat. No. 7,126,467.

(51) Int. Cl.
*G08B 19/00* (2006.01)
(52) U.S. Cl. .................. 340/521; 340/517; 340/539.26; 381/56; 381/57
(58) Field of Classification Search ................. 340/506, 340/521, 517, 539.26, 539.11, 539.27, 573.1, 340/575, 825.19, 407.1; 381/56, 57; 715/867; 705/2; 128/920
See application file for complete search history.

(56) References Cited

U.S. PATENT DOCUMENTS

| | | | |
|---|---|---|---|
| 4,091,366 A | 5/1978 | Lavallee | |
| 4,180,810 A | 12/1979 | Muncheryan | |
| 4,186,389 A | 1/1980 | Flittie | |
| 4,237,449 A | 12/1980 | Zibell | |
| 4,308,911 A | 1/1982 | Mandl | |
| 4,365,238 A | 12/1982 | Kollin | |
| 4,371,751 A | 2/1983 | Hilligoss, Jr. et al. | |
| 4,380,759 A | 4/1983 | Sulkoski et al. | |
| 4,417,235 A | 11/1983 | Del Grande | |
| 4,450,436 A | 5/1984 | Massa | |
| 4,461,927 A | 7/1984 | Olson et al. | |
| 4,617,555 A | 10/1986 | Sheiman | |
| 4,737,770 A | 4/1988 | Brunius et al. | |
| 4,897,862 A | 1/1990 | Nishihara et al. | |
| 4,935,952 A | 6/1990 | Dutra | |
| 4,951,029 A | 8/1990 | Severson | |
| 4,996,517 A | 2/1991 | Kringen et al. | |
| 5,012,223 A | 4/1991 | Griebell et al. | |
| 5,019,805 A | 5/1991 | Curl et al. | |
| 5,045,833 A | 9/1991 | Smith | |
| 5,103,216 A | 4/1992 | Sisselman | |
| 5,177,461 A | 1/1993 | Budzyna et al. | |
| D336,260 S | 6/1993 | Jensen | |

(Continued)

OTHER PUBLICATIONS

KidSmart Corporation *at* http://www.kidsmartcorp.com/ (visited Feb. 21, 2004).

(Continued)

*Primary Examiner*—Toan N Pham
(74) *Attorney, Agent, or Firm*—Dunlap, Codding & Rogers, P.C.

(57) ABSTRACT

Alarm monitors comprising conventional personal computers respond automatically to an identified alarm sound by sending a notification signal via the Internet only when a special sound monitoring program is active.

20 Claims, 9 Drawing Sheets

U.S. PATENT DOCUMENTS

| | | | |
|---|---|---|---|
| 5,278,539 | A | 1/1994 | Lauterbach et al. |
| 5,327,488 | A | 7/1994 | Garland |
| 5,349,338 | A | 9/1994 | Routman et al. |
| 5,400,246 | A | 3/1995 | Wilson et al. |
| 5,412,616 | A | 5/1995 | Gonzalez |
| 5,426,688 | A | 6/1995 | Anand |
| 5,440,301 | A | 8/1995 | Evans |
| 5,444,642 | A | 8/1995 | Montgomery et al. |
| 5,451,929 | A | 9/1995 | Adelman et al. |
| 5,452,356 | A | 9/1995 | Albert |
| 5,481,255 | A | 1/1996 | Albert et al. |
| 5,486,812 | A | 1/1996 | Todd |
| 5,543,778 | A | 8/1996 | Stouffer |
| 5,546,293 | A | 8/1996 | Moran, III |
| 5,555,876 | A | 9/1996 | Francisco, Jr. et al. |
| 5,566,339 | A | 10/1996 | Perholtz et al. |
| 5,568,535 | A | 10/1996 | Sheffer et al. |
| 5,598,456 | A | 1/1997 | Feinberg |
| 5,621,662 | A | 4/1997 | Humphries et al. |
| 5,663,714 | A | 9/1997 | Fray |
| 5,666,331 | A | 9/1997 | Kollin |
| 5,673,304 | A | 9/1997 | Connor et al. |
| 5,691,703 | A | 11/1997 | Roby et al. |
| 5,692,215 | A | 11/1997 | Kutzik et al. |
| 5,703,749 | A | 12/1997 | Prasad |
| 5,735,285 | A | 4/1998 | Albert et al. |
| 5,745,849 | A | 4/1998 | Britton |
| 5,748,072 | A | 5/1998 | Wang |
| 5,748,081 | A | 5/1998 | Lin |
| 5,793,840 | A | 8/1998 | Zhuang et al. |
| 5,805,063 | A | 9/1998 | Kackman |
| 5,883,568 | A | 3/1999 | Boyden |
| 5,889,468 | A | 3/1999 | Banga |
| 5,898,369 | A | 4/1999 | Godwin |
| 5,918,014 | A | 6/1999 | Robinson |
| 5,926,103 | A | 7/1999 | Petite |
| 5,945,924 | A | 8/1999 | Marman et al. |
| RE36,300 | E | 9/1999 | Gonzalez |
| 5,973,591 | A | 10/1999 | Schwartz et al. |
| 5,999,089 | A | 12/1999 | Carlson |
| 6,002,427 | A | 12/1999 | Kipust |
| 6,035,047 | A | 3/2000 | Lewis |
| 6,044,346 | A | 3/2000 | Ali et al. |
| 6,060,994 | A | 5/2000 | Chen |
| 6,097,308 | A | 8/2000 | Albert et al. |
| 6,145,083 | A | 11/2000 | Shaffer et al. |
| 6,151,385 | A | 11/2000 | Reich et al. |
| 6,204,761 | B1 | 3/2001 | Vanderable |
| 6,215,404 | B1 | 4/2001 | Morales |
| 6,264,614 | B1 | 7/2001 | Albert et al. |
| 6,288,715 | B1 | 9/2001 | Bain et al. |
| 6,330,499 | B1 | 12/2001 | Chou et al. |
| 6,353,449 | B1 | 3/2002 | Gregg et al. |
| 6,356,192 | B1 | 3/2002 | Menard et al. |
| 6,396,476 | B1 | 5/2002 | Bradski et al. |
| 6,400,265 | B1 | 6/2002 | Saylor et al. |
| 6,487,623 | B1 | 11/2002 | Emerson et al. |
| 6,553,100 | B1 | 4/2003 | Chen et al. |
| 6,614,348 | B2 | 9/2003 | Ciccolo et al. |
| 6,658,123 | B1 | 12/2003 | Crutcher |
| 6,685,633 | B2 | 2/2004 | Albert et al. |
| 6,693,530 | B1 | 2/2004 | Dowens et al. |
| 2004/0145467 | A1 | 7/2004 | Roby |

OTHER PUBLICATIONS

SafetyLine Institute, "Sound Power and Sound Intensity," at http://www.safetyline.wa.gov.au/institute/level2/course18/lecture53/153_04/asp (visited Sep. 24, 2003).
KFOR.com, "Standard, talking smoke alarms have little effect on kids," by Brad Edwards, at http://www.kfor.com/global/story.asp?s=1633963&ClientType=Printable, updated Feb. 6, 2004.
The Nando Times, "Is your smoke alarm loud enough?" at http://www.nandotimes.com/static/nt/images/2003/august/alarms.html (visited Sep. 4, 2003).
SeniorShops, "Sonic Boom Loud Alarm Clock," at http://www.seniorshops.com/sonicboomalarm.html (visited Jan. 13, 2003).
Sarbash Software, "Computer Security System," at http://www.sarbash.com/pro_csss.shtml (visited Sep. 7, 2002).
PRWEB Newswire, "CSSS—Computer Sound Security System," at http://www.prweb.com/releases/2001/5/prweb25104.htm, Nov. 14, 2003.
The Ezine Dot Net, "CSSS—Computer Sound Security System," by Victor Sarbash at http://theezine.net, Nov. 14, 2003.
Spy Arsenal, RoboNanny v1.00—home security monitoring tool, at http://www.spyarsenal.com/spy-microphone (visited Nov. 14, 2003).
Shareware Junction, "Access your PC—from Anywhere." at http://www.sharewarejunction.com/info.asp?ProductID=13382 (visited Sep. 24, 2003).
Borland Developer Network, "Random Images Screen Saver in Delphi," by Corbin Dunn at http://216.239.39.104/search?q=cache:ZRTxrjVq1o8J:community.borland.com (visited Oct. 28, 2003).
Symantec, "How to close open programs (including those running in the background)," at http://service1.symantec.com/SUPPORT/tsgeninfo.nst/pfdoc/199712495221?Open (last modified Oct. 21, 2003) (visited Oct. 28, 2003).
ScreenSaver Science at http://216.239.39.104/search?q=cache:jiPk8Va6T44J:gams.nist.gov (visited Oct. 28, 2003).
"The Effectiveness of the Domestic Smoke Alarm Signal," by Christine Duncan, Fire Engineering Research Report 99/5, School of Engineering, University of Canterbury, Christchurch, New Zealand, Mar. 1999.
NFPA Journal, "Fire Alarm Evacuation—Are You Ready?" by Lee Richardson, at http://216.239.41.104/search?q=cache:n4R7AEfsiU0J:www.nfpa.org , Sep. 20, 2003 (visited Oct. 27, 2003).
CAOHC, "Acoustical Consideration for Effective Emergency Alarm Systems in an Industrial Setting Part Two," by David C. Byrne, MS CCC-A, and Dennis P. Driscoll, PE, vol. 9, Issue 4, Winter 1998, at http://216.239.41.104/search?q=cache:-tqQzsWtz0J:www.caohc.org (visited Oct. 27, 2003).
Kay Elemetrics, "Advantages of CSL, Model 4300B, Hardware," at http://216.239.41.104/search?q=cache:FPAwINu5X1gJ:www.kayelemetrics.com (visited Oct. 27, 2003).
MVI Technologies Group, "Digital—Analogue real-time acquisition card," Sep. 27, 1999.
IEEE Communications Magazine, "Standards Topics Standardization on Multimedia Communications: Computer-Telephony-Integration-Related Issues," by Koichi Asatani, Jul. 1998, at http://216.239.41.104/search?q=cache:afMDoUCa410J:www.comsocorg (visited Oct. 27, 2003).
National Fire Alarm Code, pp. 72-156 and 72-157, 1999 Edition.
Electronics Catalog, pp. 309-310, Apr. 1999.
SDM Products Catalog, "Glassbreak Sensor," p. 94, Sep. 2000.
Age Matters, "Age-Matters Personal Alarm Unit," at http://www.age-matters.org/personalalarm/personal-alarm-unit.html (visited Oct. 29, 2003).
"Creating a Computer Cop—An Integrated Approach to Recognizing Human Eating Activity," by Peter Barnum, Dominic Marino, Evan Merz, Matt Pelmear and Dasun Peramunage, University of Rochester, May 2003.
"A new sound source location algorithm based on formant frequency for sound image localization," by Kenzo Obata, Kentaro Noguchi and Yoshiaki Tadokoro, IEEE International Conference on Multimedia & Expo, vol. 1, pp. 729-732.
Reliable Software, "Frequency Analyzer," at http://64.233.167.104/search?q=cache:hAWWPGF96eUJ:www.relisoft.com (visited Apr. 30, 2004).

Dan Ellis: Research Projects: "Alarm Sound Detection" at http://64.233.167.104/search?q=cache:fGthnGeSYBEJ:www.ee.columbia.edu, last updated Dec. 11, 2002 (visited Apr. 30, 2004).

Wavecom Digital Data Decoders at http://64.233.167.104/search?q=cache:1A4iES-fIS4J:ourworld.compuserve.com (visited Apr. 30, 2004).

Timex Heart Rate Monitors, "The Heart Rate Monitor Shop," at http://64.233.167.104/search?q=cache: gy19hK4ZS8J:www.heartratemonitor.co.uk (visited Apr. 20, 2004).

Sonic Boom Alarm Clock at http://www.sonicalert/com/htm/clock.htm (visted Apr. 19, 2004).

Code Blue Communications, Inc., "2nd Generation Serial Port Adapter and OEM Serial Port Adapter" at http://www.codebluecommunications.com/2nd%20Generation.htm (visited Mar. 29, 2004).

The Caregivers Marketplace at http://64.122.167.104/search?q=cache:ZHz2x728C3sJ:www.caregiversmarketplace.com/product_view.cfm? (visited Mar. 29, 2004).

University of Louisville Public Safety, "Campus Emergency Call Boxes," at http://64.233.167.104/search?q=cacheiqyRzJhThZpQJ:www.louisville.edu/admin/dps/police/phone.htm.(1996) (visted Mar. 29, 2004).

"Modular Connector Pin Assignment" at http://www.shout.net/~wildixon/telecom/rj/jackplug.gif (visited Mar. 29, 2004).

SB200ss Sonic Boom Alarm Clock at http://64.233.167.104/search?q=cache:14uCCeANexYJ:earlink.com/AC_SonicAlert.htm. (visted Apr. 15, 2004).

Fermi National Accelerator Laboratory, "Questions About Physics," Kurt Riesselmann, Fermilab, e-mail at http://www.fnal.gov/pub/inquiring/questions/waves.html, last modified Sep. 20, 2002 (visted Mar. 30, 2004).

SearchNetworking.com, "Telephone Jacks," at http://64.233.167.104/search?q=cache:hzJe—hxIJ:searchnetworking.techtarget.com/sDefinition/0..sid7_gci214238.00.html, last updated Jan. 13, 2004 (visited Mar. 29, 2004).

IMSystems, "Actitrac Activity Monitor," at http://www.imsystems.net/ActiTrac.html (visited Sep. 15, 2003).

Electronic Engineering Corporation, "Apnea Monitor," at http://www.eeconnet.com/apnea.html (visited Sep. 15, 2003).

Shareware Junction, "PC Alarm and Security System" at http://www.sharewarejunction.com/info.asp?ProductID=13382 (visited Sep. 24, 2003).

"Digital Watchdog," by Jeffrey S. Young, Forbes, vol. 157, Issue 10, p. 282, May 20, 1996.

Vicinium Systems, Inc. Brochure (2000).

An Introduction to the Analysis and Processing of Signals, 2d Ed., Paul A. Lynn. pp. 231-241, Howard S. Sams & Co., Inc., Indianapolis, Indiana (1982).

Signal and Image Processing with Neural Networks A C++ Sourcebook, Timothy Masaters, pp. 95-104 and 137-138, John Wiley & Sons, Inc. (1994).

Biomedical Digital Signal Processing, Willis J. Tompkins, Editor, pp. 220-226, 231-236 and 241-243, Prentice-Hall, Englewood Cliffs, New Jersey (1993).

Power Point Presentation of Combustion Science & Engineering, Inc., titled "Development of Smoke Allerting Device for Deaf and Hard of Hearing," Oct. 4, 2004.

" KA300TX Mini-Manual," Compu-TTY, Inc., Fort Worth, TX, available as pdf at http://www.computty.com/com/product/signdevice/ka300tx.html (visited Feb. 2006).

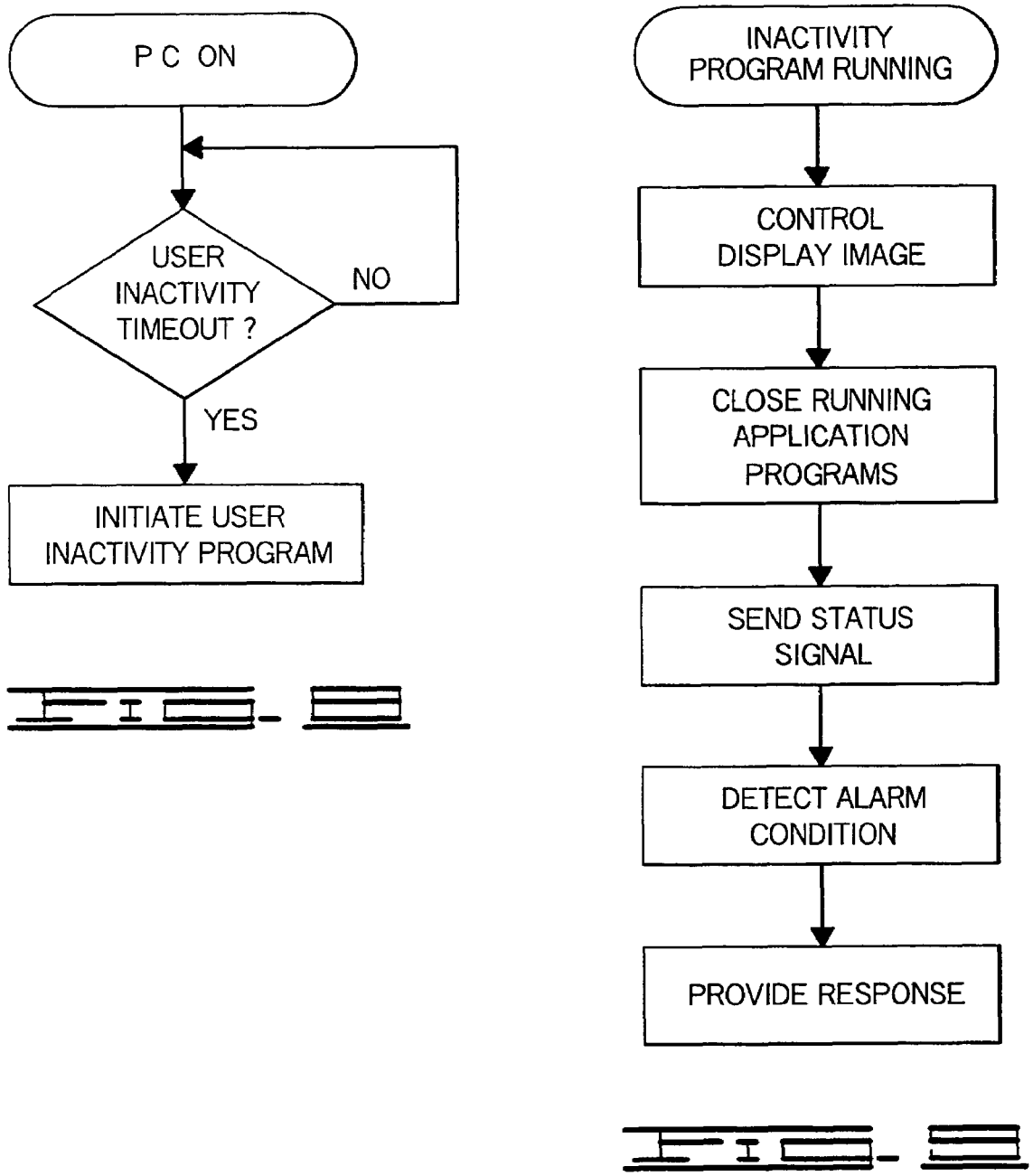

ENHANCED ALARM MONITORING USING A SOUND MONITORING SCREEN SAVER

CROSS REFERENCE TO RELATED APPLICATIONS

This application is a divisional of application Ser. No. 10/897,487 filed Jul. 23, 2004 now U.S. Pat. No. 7,126,467.

BACKGROUND OF THE INVENTION

This invention relates generally to sound monitoring methods, systems and devices useful in the home to enhance personal safety and to provide health monitoring. Hazards people try to avoid at their homes and workplaces include damaging fires and unwanted intruders such as burglars. These hazards cannot always be avoided, but damage from them can be limited if prompt notification is given when they occur. At least one embodiment of this invention relates more particularly to methods, systems and devices that provide an enhanced alarm and means of waking children and the hearing impaired including the elderly in response to an emergency such as a fire. In other embodiments the invention provides safety and security monitoring and in yet other embodiments the invention provides health monitoring for a large number of chronic diseases. Each of these areas, including systems using a personal computer, is discussed below.

Smoke Alarm

The annual "cost" of residential fires in the U.S. includes billions of dollars of property damage, and thousands of deaths and life-threatening injuries. This occurs even though there are smoke alarms in most of the U.S. households and small businesses. The annual death rate is heavily biased toward the young and the old.

It is now understood that the audio alarm used in standard smoke detectors is simply not always effective for awakening pre-teen children. Many children under the age of 13 sleep so soundly, especially in the first two hours of sleep, that a smoke alarm may not be loud enough to wake them. Smoke detectors have an intensity of about 80 decibels and studies have shown that in deep sleep, only one in 20 children will awaken to a sound of 120 decibels.

Deaf and elderly people with hearing impairments, and anyone who wears or needs a hearing aid, are at a significantly increased risk of not awakening to the smoke alarm sounds. In fact, most smoke alarms produce their audio alert in the 3 to 4 KHz range which is in the zone of age-related hearing deficits.

The problem is compounded by the fact that many residences have smoke detectors outside of bedrooms. This is actually recommended to provide as early a warning as possible. For example, by the time a fire reaches a bedroom and a sleeping resident is awakened by an in-room detector, the fire may be widespread making it too late to escape. (This problem can be avoided in new construction where communicating wired or wireless smoke detectors are designed so that when any one alarm sounds, they all sound, and they can therefore be placed both in and outside bedrooms.) Additionally, fire experts suggest that bedroom doors be closed at night to act as functional fire and smoke barriers which can provide an extra margin of escape time. This sounds good but it presents a serious physics problem. Sound, like other radiated energy (e.g., heat and light), obeys the Inverse Power Law. The Inverse Power Law means that the sound intensity decreases proportionately to the square of the distance from the source. So, for example, a typical 85 dB smoke detector signal that must pass through a wall or closed door and traverse the distance across and down to a sleeping child or adult is greatly diminished in intensity, thereby also diminishing the chance to wake a child or hearing impaired adult.

The KidSmart™ smoke detector addresses this problem by having a detector above the child's bed and utilizing a downward, directional speaker to try to increase the sound intensity at the child. While this improves the chances of waking the child, using in-bedroom smoke detectors to deliver a louder alert due to proximity is also not desirable, as discussed above, because there must be smoke present in the room prior to the alarm's sounding, thus reducing the time available for escape.

Remote monitoring of smoke detectors is also available with specialized fire detection systems and with most security systems, but it is expensive and therefore not generally used for middle and low income housing including single family and multi-family buildings.

There is a need for enhanced fire alarms that are more effective for waking sleeping children, the elderly and the hearing impaired, as well as a need for simple and inexpensive monitoring of home fire alarms.

Safety and Security Monitors

When individuals are alone or sleeping, they can feel especially vulnerable. For example, most burglaries occur at night when people are sleeping. Elderly and handicapped people living alone can fall or have an accident and not get assistance for extended periods of time. "Latch-key" children can have an accident on the way home from school and it may go unnoticed until after the parents get home from work. Not only are these situations dangerous, but the potential for such situations also causes significant anxiety.

To reduce the dangers and relieve some of the related anxiety, a number of home security systems have been brought to the market. Some of these systems include motion detectors that attempt to differentiate between humans and pets, glass-break detectors, door and window contacts, and even video surveillance cameras. Also, wireless pendant security transmitters are marketed to allow the elderly, in a sudden emergency event such as a fall or a heart attack, to simply push a button to notify emergency help. These types of electronic instruments and associated monitoring services can be quite expensive, so there is a need for monitoring services that are readily available to middle and lower income levels.

Additionally, monitoring services are not generally available for working parents checking on their school children. Parents often require their children to call, e-mail or instant message them at work once they get home from school, and this is very helpful. However, it would be preferable to automatically notify the parent when the situation occurs; there is consumer demand and a real need for such a notification system.

Health Monitor

The long-term value of disease management is now becoming clear, especially for people who have one or more chronic conditions or diseases. Disease management programs designed to get the optimum treatment to the patient as early as possible can improve health care quality as well as save costs. Such program advantages apply to both Medicare and private sector commercial health care markets, thus offering a substantial return on investment for our nation's seniors.

Baby boomers may break an already strained healthcare delivery system unless a system becomes available that allows for home monitoring, thus enabling home care and disease management. While it is economically beneficial to find ways to keep seniors with chronic ailments out of the hospital, other health problems could also benefit from home monitoring. For example, asthma is a chronic inflammatory condition which can be a life-threatening disease if not properly managed. Nighttime monitoring can warn a patient or parent of an upcoming attack before more acute symptoms appear. Similarly, obstructive sleep apnea and emphysema, which occur in both children and adults in large numbers, would benefit by nighttime monitoring.

There is a need for equipment and services that can inexpensively monitor health signs and provide appropriate responses.

Computer Applications

Very sophisticated monitoring systems include computer controlled home and commercial building environmental, safety and security systems that provide both local and remote signals to indicate a detected status or alarm condition. Implementing these systems may require running dedicated wire throughout a building while connecting sensors and controllers. Various other types of installations, including ones with wireless radio signal communication and ones using existing wire systems, can also be provided.

Despite the existing systems, there is still the need for a simplified, sound-detecting, remote notification type of alarm monitoring that requires little or no additional hardware beyond what is already at a location where the present invention is to be used, that automatically activates and deactivates itself, and that enables a remote site to know whether it is operating properly. There is a need for more cost effective alarm monitoring to be available to most any home or business having wired or wireless Internet access.

SUMMARY OF THE INVENTION

The present invention provides improved devices and systems for monitoring and responding to emergency, safety, and health conditions which meet the needs described above. The present invention, in brief, monitors ambient sound to detect alarm conditions and provide appropriate responses. The invention utilizes a device, preferably a bedside device and/or a personal computer and can be used in a number of different configurations and applications. The three major applications utilizing a bedside device are fire alarm detection, safety and security monitors, and health monitors, each of which is summarized separately below. Use of a personal computer to perform many of these functions is also summarized separately.

Fire Alarm Detection

Many people, especially children and those with hearing impairments, do not awaken from the alarm of a residential smoke detector. A method of this invention for waking an individual in response to an audible alarm from a pre-existing alarm device involves the following steps. A bedside alarm unit is operated which comprises a microphone for receiving ambient sounds and a microprocessor for detecting from sounds received, an alarm signal from a pre-existing alarm device. In response to detecting an alarm signal, the unit activates a waking device. "Pre-existing alarm device" refers to an audible alarm device that is, or could be, already used to provide an alarm. For example, in one embodiment, the pre-existing alarm device is a smoke detector. An audible alarm from the smoke detector is detected using the bedside unit which controls a switch for supplying power to a waking device. Upon detection of the smoke detector alarm, the unit switches on a supply of power to the waking device, thus activating it. Examples of waking devices include, but are not limited to, a bedside very loud (100 dB or greater) audible alert, bed shaking device, light and a speaker giving verbal instructions. A waking system can be utilized that combines two or more waking devices.

In other embodiments, the sound monitoring unit further includes a communications port. The unit additionally generates notification signals when a smoke detector alarm is determined and uses the communications port via wired or wireless means to send the signals to local emergency personnel, or to a monitoring service, preferably an Internet site.

In yet another embodiment, motion detectors are used to determine whether an individual remains within the room after a smoke detector alarm is determined. An infrared motion sensor may be built into the bedside unit and communicate directly to the microprocessor. Alternatively, the bedside sound monitoring unit further comprises a receiver for receiving signals from a wireless motion sensor positioned to detect motion within the room containing the bedside sound monitoring unit. In another preferred embodiment, the motion detector is a load sensor positioned in the bed. The load sensor can be wired directly to the bedside unit, or can communicate wirelessly with a receiver in the bedside unit. After a smoke alarm is determined, the sound monitoring unit further determines from the motion detector signals whether an individual remains within the room and preferably generates and sends notification to appropriate personnel regarding whether an individual remains within the room. Nonlimiting examples of appropriate personnel include a monitoring service or local emergency personnel.

A fire alarm system of this invention includes an audible fire alarm, a bedside sound monitoring unit and a waking device or waking system. The sound monitoring unit comprises a microphone, a microprocessor to identify the fire alarm, and a switch controlling supply of power to the waking device or system to be switched on in response to the fire alarm.

A memory device of this invention comprises a memory device for a microprocessor in a bedside alarm monitoring unit and includes a memory substrate and a monitoring means disposed on the memory substrate. The monitoring means includes a means encoded on the substrate for determining when sound received through a microphone of the bedside unit is a fire alarm sound and a means encoded on the substrate for cooperatively functioning with a switching device to activate a waking device when a fire alarm is determined.

In one embodiment the ANSI/ISO smoke alarm signature is stored in the memory and used to identify the smoke alarm from ambient sounds using conventional digital signal processing techniques such as spectral analysis, time-frequency analysis, matched filters, correlation analysis and neural networks.

In another embodiment, the unit "learns" the signal generated by a particular alarming device by having the user generate a test signal which is received then by the microphone and stored in the memory as a test signal signature. Signal analysis techniques described above are used to identify the alarm.

Home Safety and Security Monitor

Home safety and security monitoring methods and systems of this invention utilize a sound monitoring unit comprising a microphone, microprocessor and a communications port. The microprocessor determines, from sounds received by the microphone, when a pre-existing home security alarm is sounding, and in response thereto generates and sends response signals out the communications port. A "pre-existing home security alarm" refers to an audible alarm device that is, or could be, already used to provide an alarm in response to a security breach. In one embodiment, the home security alarm monitor is present in a bedside unit additionally comprising the fire alarm monitor and the waking device activator or system basically as described above but modified as necessary to accommodate the home safety and security equipment.

Examples of audible security alarms that may be used with the present invention include, but are not limited to, personal alert pendants including pins and wristbands, door-open sensors, window-open sensors, glass-breaking sensors and motion detectors. Response signals are sent through the communications port either wirelessly, through a jack to a standard phone system, or through a broadband Internet connection, to deliver an alert to an individual, local emergency personnel, a monitoring service or an Internet site comprising a network operating center monitoring service.

While useful for detecting emergency situations, the unit can also be used to provide security monitoring in non-emergency situations. For example, the unit can detect the sound from a door-open sensor and notify working parents that their child has arrived home from school. In one embodiment, parental notification is given by e-mail or Internet instant messaging.

In another embodiment, a bedside sound monitoring unit is operated to detect breathing sounds and determine if the sounds include a breathing pattern representing a condition requiring a response. By operating the bedside unit, response signals are generated and sent out the communications port when a response is required.

A home security system of this invention includes an audible security alarm and a sound monitoring unit. The sound monitoring unit comprises a microphone, a microprocessor to identify the security alarm, and a communications port for sending a notification signal when the security alarm is identified. In another embodiment, the home security system further comprises the audible fire alarm and the waking device previously described, but modified as necessary to implement the home security system.

A home security system memory device of this invention comprises a memory device for a microprocessor in a security alarm monitoring unit and includes a memory substrate and a monitoring means disposed on the memory substrate. The monitoring means includes means encoded on the substrate for determining when sound received through a microphone of the unit is a security alarm sound and means encoded on the substrate for communicating responsive signals when a security alarm is determined.

Health Monitor

A method of this invention for monitoring health indicating parameters of an individual using a bedside unit comprises the following steps. A bedside monitoring unit is operated which comprises a microphone, microprocessor and a communications port. The unit operates to detect sounds, which include health indicating parameters, received by the microphone. The unit then relays these health indicating parameters to a medical monitoring service. In one embodiment the health indicating parameters are breathing related and preferably include breathing rate, breathing sound frequency spectrum, snoring and coughing.

In another embodiment, the bedside unit additionally includes receivers to specifically receive signals from medical monitoring devices, nonlimiting examples of which include devices such as accelerometers, load sensors, and wireless chest strap heart monitors. In this embodiment the bedside unit delivers the additional signals from the electroacoustic, wired and wireless devices through the communications port to the medical monitoring service.

The health monitor of this invention includes a monitoring program stored within a microprocessor of a bedside unit. The program includes instructional signals for relaying sound received by a microphone of the bedside unit, through a communications port of the unit, and to a medical monitoring service. In other embodiments, the monitoring program includes instructional signals for screening the sounds received by the microphone to determine those sounds representing health indicating parameters, and also instructional signals for processing and evaluating the sound received.

In another embodiment, the home health monitoring system further comprises the audible fire alarm and the waking device previously described. The bedside unit additionally comprises the fire alarm monitor and a waking device activator as described above, but modified as necessary to implement the health monitoring system. In yet another embodiment, the monitoring system comprises programming enabling the bedside unit to detect and differentiate multiple sounds, signals and alarms related to fire, safety, security and health monitoring and to provide a specific response to each.

A method of this invention for providing medical monitoring service comprises receiving at a medical monitoring service location signals from the bedside unit described above and analyzing those signals to determine if a medical response is required. The medical monitoring service employs health experts for both long-term and short-term evaluation of the monitored data. If determined necessary, a medical response is provided which may comprise notifying the monitored person's doctor or emergency personnel.

Personal Computer

The present invention also provides a novel and improved sound monitoring method, system and device useful with conventional personal computers including, but not limited to, desktop, laptop, palmtop and smart phone units. Implementation is similar to that for the bedside unit described above but modified to use a sound monitoring program and a personal computer to respond automatically to an identified alarm sound by sending a notification signal via the Internet.

This embodiment of the present invention can be used anywhere there are a sound source, such as one that indicates an alarm event, and a computer that has its own microphone or other sound-detecting device. Preferably such computer has access to a global communication network, such as the Internet or its World Wide Web. For a place that already has this equipment, no additional hardware is needed to implement the method of the present invention. Of course, other hardware can be obtained and used in implementing the present invention.

One definition of the computer application of the present invention is as a method for using a personal computer to monitor an area for a predetermined audible alarm signal generated by a pre-existing alarm device, comprising: operating a specialized sound monitoring program in a personal computer having conventional system software and hardware including a microphone, sound signal digitizing capability, and a communications port, wherein the specialized sound monitoring program is compatible with the conventional hardware and system software; and by operating the specialized sound monitoring program, detecting from sounds received by the microphone of the personal computer when alarm conditions exist and in response thereto generating and sending response signals out the communications port of the personal computer. Nonlimiting examples of personal computers include desk top computers, laptop and notebook computers, handheld personal computers, palmtop and pocket computers, personal digital assistants and smart phones. The sound monitoring program can be operated in the foreground or background of the personal computer or as an inactivity program or screen saver program and can close or override other running application programs in the personal computer when alarm conditions are detected.

Another definition of the computer application of the present invention is as a method for detecting an audible alarm generated by a pre-existing alarm device by monitoring sound with a personal computer, comprising: running a specialized sound monitoring program in the personal computer; using the running sound monitoring program, detecting sound received by a microphone of the personal computer, and determining if detected sound represents an alarm from a pre-existing alarm device requiring a response; and using the running sound monitoring program, providing a response when a response is required. The sound monitoring program is preferably a screen saver operated only during a computer input inactivity period. The pre-existing alarm device includes, but is not limited to, fire or smoke alarms, severe weather alarms, burglar alarms, door-open sensors and personal alarms. Providing a response can include generating and sending alarm indicating signals to an Internet site having an Internet address encoded within the sound monitoring program using e-mail or Internet instant messaging. If utilizing Internet instant messaging to alert a Central Monitoring Service, the service will also know when the remote acoustic monitoring program is active. The method can further comprise downloading, from an Internet Web site, the sound monitoring program into the personal computer and providing a response can include sending an alarm notification signal to that Internet Web site. Another feature can include communicating from the Internet site to a telecommunication number or e-mail address designated for the personal computer. Providing a response can also include generating and playing an acoustic alert on the speaker(s) of the personal computer.

Yet another definition of the computer application of the present invention is as a method for monitoring health indicating parameters of an individual, comprising the following steps. A specialized sound monitoring program is run in a personal computer having conventional system software and hardware including a microphone and communications port. Using the running sound monitoring program, the personal computer detects sounds comprising health indicating parameters received by the microphone of the personal computer. Using the communications port of the personal computer, the health indicating parameters are relayed to a medical monitoring service. Nonlimiting examples of health indicating parameters that can be monitored using the present invention include breathing-related parameters such as breathing rate, breathing sound frequency spectrum, snoring and coughing.

A definition of the present invention specific to sensing a smoke detector alarm using a screen saver program calls for a method for monitoring sound with a personal computer, comprising: running a sound monitoring screen saver program in a personal computer in response to a timeout event occurring because an externally generated input is not received by the personal computer within a predetermined time period during operation of the personal computer; from time to time during the running of the sound monitoring screen saver program, accessing from the personal computer an Internet site and sending to the accessed Internet site a predetermined signal if the computer is properly functioning under operation of the running screen saver program; receiving ambient sound at a microphone of the personal computer; determining with the running screen saver program whether ambient sound received at the microphone includes an alarm sound from a residential smoke detector providing a sound output in accordance with a predetermined standard; and accessing from the personal computer the Internet site when an alarm sound is determined and sending an alarm indicating signal to the accessed Internet site.

The computer application of the present invention can also be defined as a method for providing for alarm monitoring in a residence, comprising: receiving at an Internet site a program load command from a conventional personal computer at a residence; transmitting from the Internet site to the personal computer, in response to the program load command, an alarm sound monitoring program for installation on the personal computer; and receiving at the Internet site an alarm indicating signal sent from the personal computer when the personal computer detects an alarm condition using the sound monitoring program and transmitting a notification signal from the Internet site in response. This can further comprise: monitoring at the Internet site the operational status of the personal computer, including receiving status signals sent from the personal computer to the Internet site, and transmitting a status notification from the Internet site when status signals are not received at the Internet site during a monitoring period; and/or updating the sound monitoring program by transmitting from the Internet site to the personal computer digitally encoded advertising indicia signals such that the alarm sound monitoring program periodically causes advertising indicia to be displayed through a display of the personal computer. The alarm sound monitoring program can additionally be installed as a screen saver program, or more preferably, the default screen saver program on the personal computer and can provide a list of standardized alarm sounds to be selected from or a learning mode during initial setup allowing the alarm sound to be activated, detected and identified as such.

The present invention also provides an alarm monitor, comprising: a conventional personal computer including a microphone, a memory, a communication port, a display and system software; and a sound monitoring program stored in the memory. The sound monitoring program includes: first instructional signals encoded on the memory for cooperatively functioning with the system software to determine when sound received through the microphone of the personal computer is an alarm sound; and second instructional signals encoded on the memory for cooperatively functioning with the system software to communicate responsive signals from the personal computer when an alarm sound is determined. The sound monitoring program can be a screen saver including third instructional signals encoded on the memory for cooperatively functioning with the system software to control what indicia are displayed on the display of the personal computer during user inactivity periods. These additional instructional signals can include signals defining advertising indicia to be displayed on the display of the personal computer. The sound monitoring screen saver program can also include other instructional signals encoded on the memory for cooperatively functioning with the system software to close or override other running application programs in the personal computer when an alarm sound is determined. The sound monitoring program can further include still other instructional signals encoded on the memory for cooperatively functioning with the system software to generate status signals to be transmitted to a remote location to indicate operational status of the personal computer when the sound monitoring program is in operation in the personal computer. The invention can also be defined as a memory device comprising a memory substrate and the aforementioned program encoded thereon.

With the foregoing, it is possible to provide improved alarm responses and to provide low cost, easily implemented safety, security or health monitoring. Other features and advantages of the present invention will be readily apparent to those skilled in the art when the following description of the preferred embodiments is read in conjunction with the accompanying drawings.

BRIEF DESCRIPTION OF THE DRAWINGS

FIG. 8 is a flow diagram of programming for the user's personal computer to obtain operation of an inactivity program of the present invention.

FIG. 9 is a flow diagram of programming for the inactivity program.

DETAILED DESCRIPTION OF THE INVENTION

The present invention utilizes existing acoustic signal analysis technology which allows, for example, the detection of alarms such as the ANSI/ISO standard smoke alarm signal. This technology can also identify any specific acoustic signal including personal alert pendants or audio door-open sensors, thus providing a platform, preferably at the bedside, for many personal safety and security monitoring services. This technology is then combined with one or more existing technologies such as, for example, an enhanced waking device for the hearing impaired, a personal computer, and a wired or wireless telephone, Internet or e-mail communication device activated by the sensing of the specific acoustic signal. Home health monitoring is provided by audio monitoring as well as by monitoring for other signals from wired or wireless devices such as heart rate monitors. The three major application categories are fire alarm detection, safety and security monitors, and health monitors, each of which is described in detail below. Configuration using a personal computer is described lastly. While each category is described separately, it is understood that multiple sounds from all categories can be monitored simultaneously using a single unit, and specific responses are generated for each monitored sound detected.

Fire Alarm Detection

An alarm system of this invention comprises a unit having a microphone for receiving ambient sounds and a microprocessor for detecting from sounds received, an alarm signal from a pre-existing alarm device, and in response thereto, activating a waking device. A device in accordance with the present invention is represented in FIG. 1.

Figure 1:
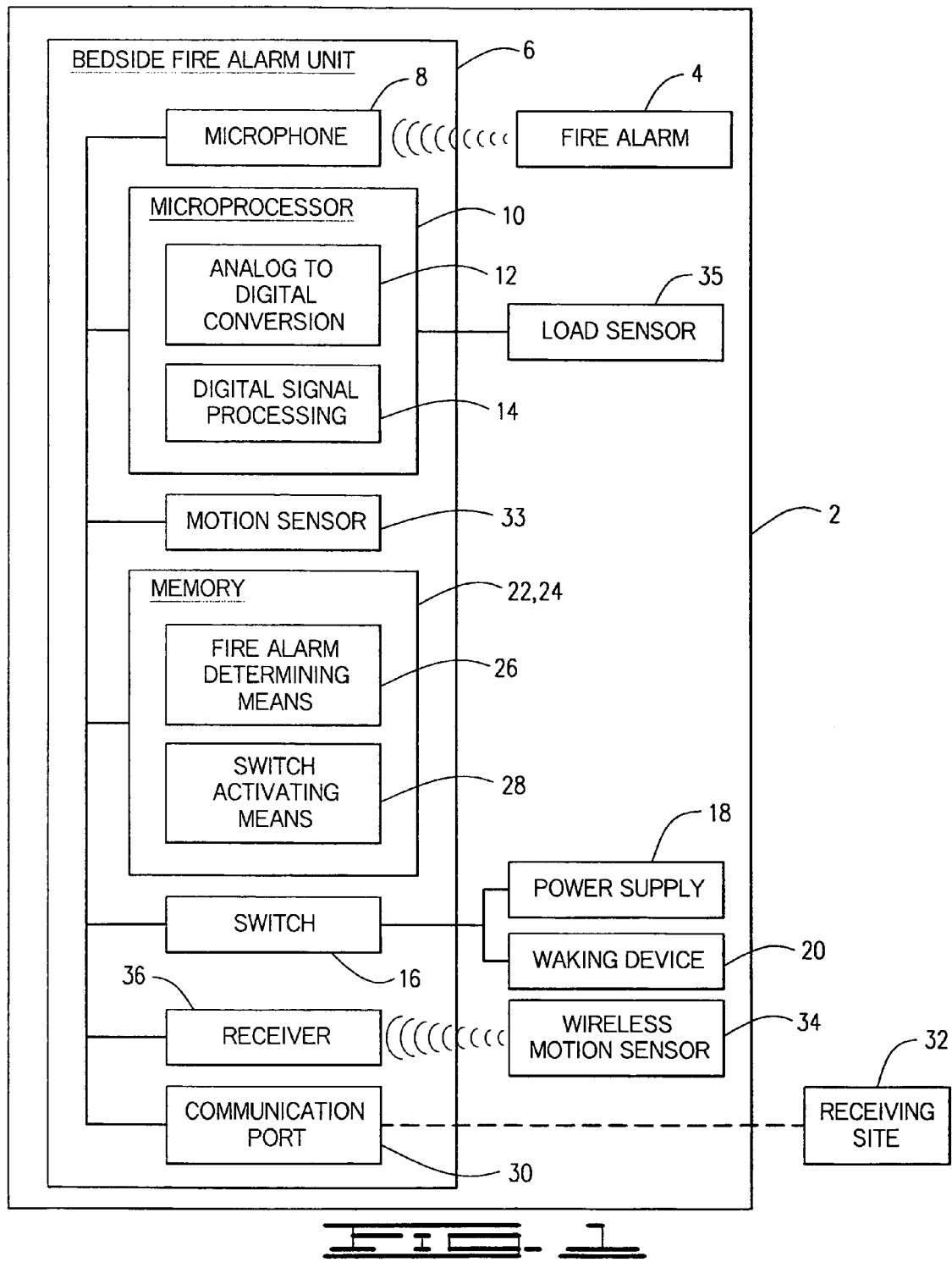
FIG. 1 is a block diagram of a smoke alarm monitoring and waking system of the present invention.

Referring to FIG. 1, a fire alarm system 2 of this invention includes a sound emitting fire alarm 4 and a bedside unit 6. The bedside unit 6 "listens" for a fire alarm, such as the traditional acoustic ANSI/ISO smoke alarm, by combining a microphone 8 with a microprocessor 10 used to implement analog to digital conversion 12 and a digital signal processing 14. Upon detecting the alarm 4, the microprocessor 10 activates a switch 16 controlling a supply of power 18 to a waking device 20. The microprocessor 10 utilizes a memory 22 which provides the storage substrate 24 for a fire alarm determining means 26 and a switch activating means 28. Preferably the unit includes communications port 30 providing the ability to communicate the smoke detection via wired or wireless means to a receiving site 32. In one embodiment, the bedside unit detects movement in the room using a motion sensor 33 included as an integral part of the bedside unit. A wired load sensor 35 placed in the bed can also be used to detect whether a person remains in bed. Optionally, a wireless motion sensor 34 external to the bedside unit can be positioned to detect motion in the room, and a receiver 36 is included within the unit for receiving signals from the wireless motion sensor.

Examples of waking devices that can be used to awaken the individual(s) in the room include, but are not limited to, a very loud alarm (100 dB or louder), bed shaking, a strobe light and loud voice instructions directing them to evacuate. The invention may be implemented as a stand-alone bedside unit, alarm clock, telephone or lamp. The system can have both AC and 24 hours of battery back-up power so that it meets the NFPA National Fire Alarm Code for fire monitoring systems. Additional features include technology such as an integrated motion sensor 33 and an in-bed load sensor 35. Both sensors may be wired or wireless, but preferably the motion sensor is integrated within the unit. Receiver 36 is included if using an external wireless motion sensor 34. Such additional features enable the bedside unit to detect if the individual(s) in the room get out of bed and whether they exit the room. This information is communicated directly to emergency personnel (e.g., firemen arriving at the scene) or to a monitoring center. This latter feature is useful not only in a single-family residence but also in hotels/motels, nursing homes, apartment buildings and residential, particularly multi-story residential institutions.

Non-limiting examples of fire detector alarms 4 include residential smoke detectors, heat detectors, and carbon monoxide detectors. Non-limiting alarm examples include smoke detectors providing single tone signals that are pulsed on and off, such as tones within the frequency range between 1 kilohertz and 4 kilohertz and with a pulse modulation rate between 3 and 8 hertz. The smoke detector used is preferably one that provides a predetermined sound output such as in accordance with the National Fire Alarm Code three-pulse code known in the art.

"Listening" for the smoke alarm is accomplished using the microphone 8 and microprocessor 10 utilizing digital acoustic signal recognition technology. Matched filtering technology can be used and such filter algorithms prevent or minimize the occurrence of false alarms from noise. The matched filter acts as a type of fingerprint-matching to identify whether the signals passed match the frequencies and pulse pattern of the smoke alarm being monitored.

For example, the microphone first converts sounds into voltage or other electrical signals. The electrical signals are then processed by an analog to digital conversion 12 by scanning, measuring and splitting the electrical signals into discrete values, thus producing a digital pattern representing the sound received at the microphone. The digitized sound is input to the digital signal processing function 14 of the microprocessor. Here the microprocessor may use digital high pass and low pass filters to pass some frequency regions through unattenuated while significantly attenuating others, thus screening out the ambient noise level due to air conditioning, telephones, etc., from the alarm frequency monitored. The microprocessor then compares using a matched filter, cross correlation or a neural network the pattern of real time digital values to a pattern stored in memory 22 representing the particular smoke alarm monitored and, utilizing the fire alarm determining means 26 encoded on the memory substrate 24 of the microprocessor, determines if the smoke alarm is detected in the sounds received by the microphone.

Figure 2:
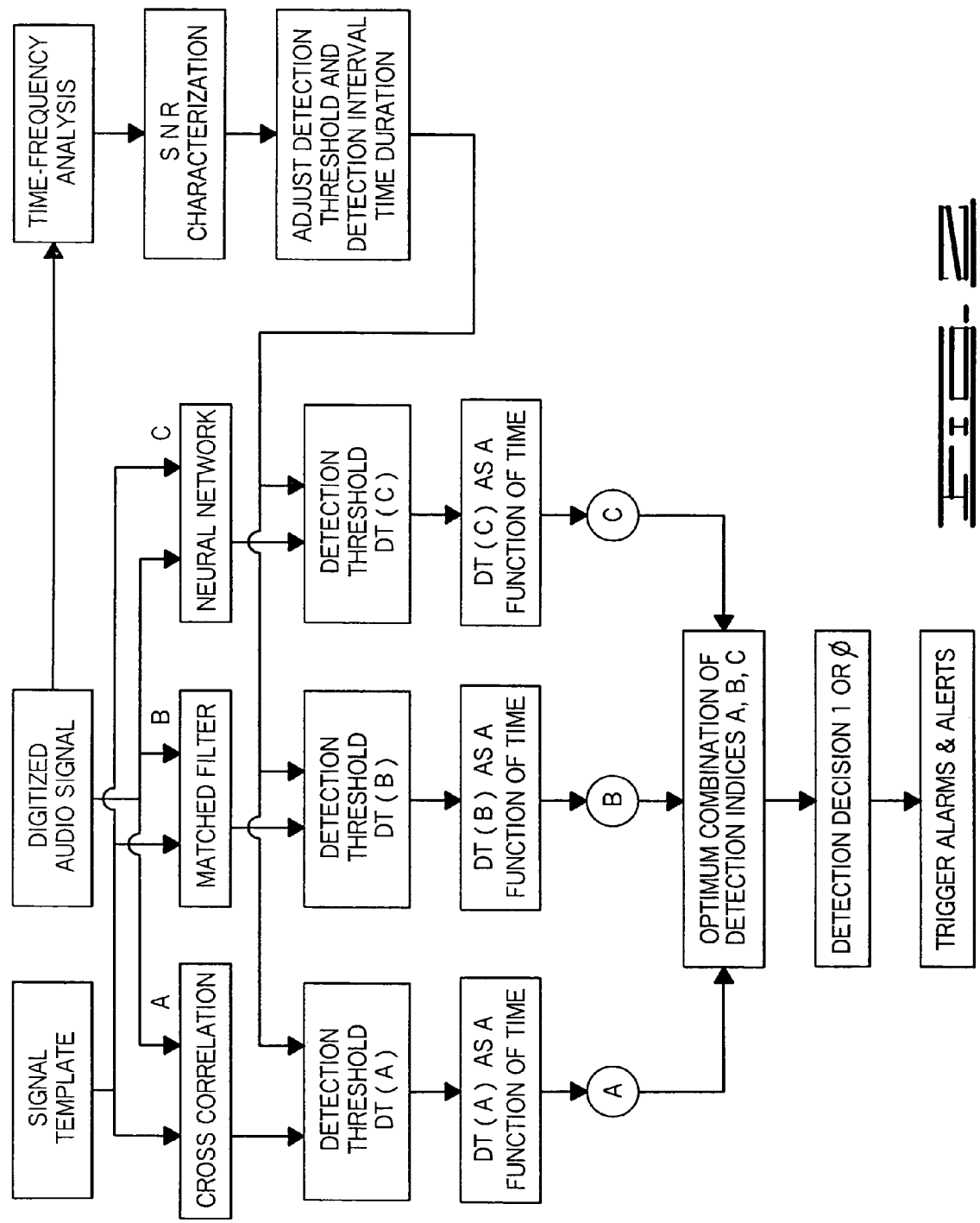
FIG. 2 is a flow diagram of programming for alarm sound recognition.

Preferably, the digital signal processing comprises logic steps similar to the flow diagram of programming for alarm sound recognition shown in FIG. 2. A time-frequency analysis of the digitized audio signals can be implemented using overlapping Fast Fourier Transforms (FFTs), Wigner-Ville Distribution, Gabor transform, wavelet analysis or other suitable techniques to characterize the signal and the noise (i.e., the signal-to-noise ratio SNR). The signals are also compared to the pattern stored in memory representing the particular smoke alarm monitored. This analysis preferably uses one or more of the following techniques to determine detection thresholds: cross-correlation, matched filtering and neural networks. The detection thresholds thus determined are combined with the time frequency analysis results to produce detection thresholds as a function of time. By monitoring and analyzing sound continuously, the detection thresholds can be adapted to the changing background noise thereby optimizing the audio alarm detection in any environment despite varying noise sources and levels. Additionally, multiple patterns can be stored in memory, thus providing simultaneous monitoring for separate sound patterns with a unique response for each.

For example, an alarm probability is estimated and can be visualized as a three dimensional surface where the accuracy of detection is plotted against SNR and the duration of detection time interval. The duration of time interval is preferably varied dynamically and adaptively in response to changing SNR in order to maintain optimum detection of audio alarms. The lower the SNR, the longer the detection interval must be to make sure the alarm is present. The minimum time interval is the duration of one period of the repetitive alarm signal. While digital audio filter and detection programming and circuitry are continually being advanced, such as with the use of neural networks, etc., the technology is commercially available and generally well known to those skilled in the art.

The frequencies and pattern of the alarm to be monitored can be encoded in the fire alarm determining means 26, or can be "learned" by activating the alarm for setup purposes such that the sound is detected by the unit in a learning mode and identified as indicating an alarm event. For example, the bedside unit may be set to "learning mode." In this mode the unit analyzes ambient noise or sound. The audio alarm to be monitored is then triggered. The unit analyzes and then stores the resulting audio alarm template. Using the template and the continuous sound sampling and analysis described above, the unit begins monitoring. Preferably the alarm sound to be monitored, whether selected or "learned," can be reset at any time and is not restricted to the sound selected during initial setup. A single or multiple alarm sound templates can be monitored simultaneously allowing for different responses to each detected alarm sound.

Upon detecting an alarm, the switch activating means 28 encoded on the memory substrate 24 dictates activation and method of activation of switch 16 to allow power supply 18 to power the waking device 20. Generally power supply 18 is the electrical power to the house accessed by an electrical socket. However, other power including battery backup power can also be utilized. A variety of waking devices 20 can be used including, for example, the alarm systems of a SonicBoom™ Alarm Clock available from Sonic Alert, Inc., of Troy, Mich. The SonicBoom™ Alarm Clock is designed to awaken the hearing impaired at a pre-selected time. It has a 100 dB alarm, an optional mechanical bed shaker/vibrator (with built-in temperature sensor to protect the unit against overheating) which is placed under the pillow or between a mattress and box springs, and an outlet that will cause a connected bedside lamp to flash thereby producing a strobe effect. The bed shaker/vibrator is plugged into the vibrator outlet on the back of the Sonic Boom™ Alarm Clock.

One embodiment of the present invention combines enhanced alarm mechanisms or waking devices, such as those in the Sonic Boom™ Alarm Clock, with a microphone and a microprocessor in a bedside unit as described above to detect an audible alarm from a residential smoke detector. A major advantage of this system is that a smoke detector can be placed outside the bedroom, thus allowing detection of a fire before it enters the bedroom. An individual sleeping in the bedroom need not be concerned about whether the outer smoke detector alarm will awaken him or her; the smoke detector alarm need only be sensed by the bedside unit which will then activate enhanced waking devices and wake the sleeping individual. If there is concern that the unit may not detect a distant smoke detector alarm, another embodiment includes a repeater to relay sound. A non-limiting example is a conventional baby monitor positioned in a house to relay sound from a smoke detector to the microphone of the bedside unit.

Other enhanced waking devices can be employed such as a blast of air, water spray or strobe light. For example, the Gentex photoelectric residential smoke alarm incorporates a 177 candela strobe light that flashes 60 times per minute and is available from Sound Clarity, Inc., of Iowa City, Iowa. One embodiment of the present invention combines such a strobe light with the bedside unit described above. Detection of the smoke detector alarm activates the strobe light. Such enhanced waking devices bring multi-modality and "intensive" stimulation to awaken the children and the hearing impaired to an emergency such as a fire, while again allowing more time for escape by locating the actual smoke detector outside the bedroom.

In a preferred mode, the bedside unit contains sensor capability that can detect weight and movement. Motion detectors and load/pressure sensors are readily available and come in several different kinds. Basic photo-sensor types emit a light beam which triggers the alarm whenever anyone interrupts the beam. This type can be mounted to detect motion away from the bed. More sophisticated passive infrared (PIR)

detectors do not emit any energy on their own, but detect infrared energy (heat) emitted in the environment. This type of motion detector can be aimed at the bed area to detect whether the child or adult is still in bed. Alternatively, a load or pressure sensor may be placed under the mattress to detect the presence of the child or adult still in bed. Preferably this valuable information is transmitted to the emergency personnel.

This information is considered invaluable in saving lives and is important in situations other than the home. Using the unit and system described above, status and location information on people can be determined in any building, e.g., a multi-story residential or office facility. In a hotel or dormitory, occupancy and in-bed status can be transmitted on a room-by-room basis in an emergency situation.

In another preferred mode the bedside unit can initiate verbal instructions once it is detected that the child or adult is out of bed. The verbal instructions are preferably a prerecorded message stating that a fire has been detected and giving appropriate guidance or instructions.

Another optional feature of this invention is an infrared (IR) sensor to detect heat behind a door. Fire experts advise holding the back of your hand to a door to detect fire on the other side; however, the system of this invention can perform this detection automatically and advise exit via an alternative route. Optionally, the bedside unit contains a flashlight to illuminate the room and exit path and additionally includes batteries so the units can function for 24 hours without AC power and can meet the National Fire Code for alerting devices.

In another preferred embodiment the bedside unit further comprises a communications port 30 and can generate and send an alarm message through communications port 30 to a receiving site 32. For example, the bedside unit can further comprise an RJ-11 jack that can be connected to a standard phone system in order to send an alert(s) to the fire department when sensing a smoke alarm. Alternatively, the bedside device can send a wired or wireless fire alarm notification in response to a smoke detector alert to a network operating center monitoring station, which will immediately forward it to the appropriate fire department. A variety of communication ports and their setup and functioning are well known to those skilled in the art.

Home Safety and Security Monitor

Another embodiment of the present invention is geared toward providing home safety and security. Home safety and security monitoring systems of this invention utilize a unit comprising a microphone, microprocessor and means to connect to a communications system wherein the equipment is basically as previously described but modified as necessary to implement the home safety and security functions. The microprocessor detects when a safety or security alarm is sounding, and in response thereto delivers an alert to an individual, emergency personnel or a network operating center monitoring service. The present invention utilizes previously described digital signal analysis technology modified as necessary to identify one or more specific acoustic signals including, but not limited to, acoustic signals from personal alert pendants, pins and wristbands, door open sensors, window open sensors, glass breaking sensors and motion detectors.

Figure 3:
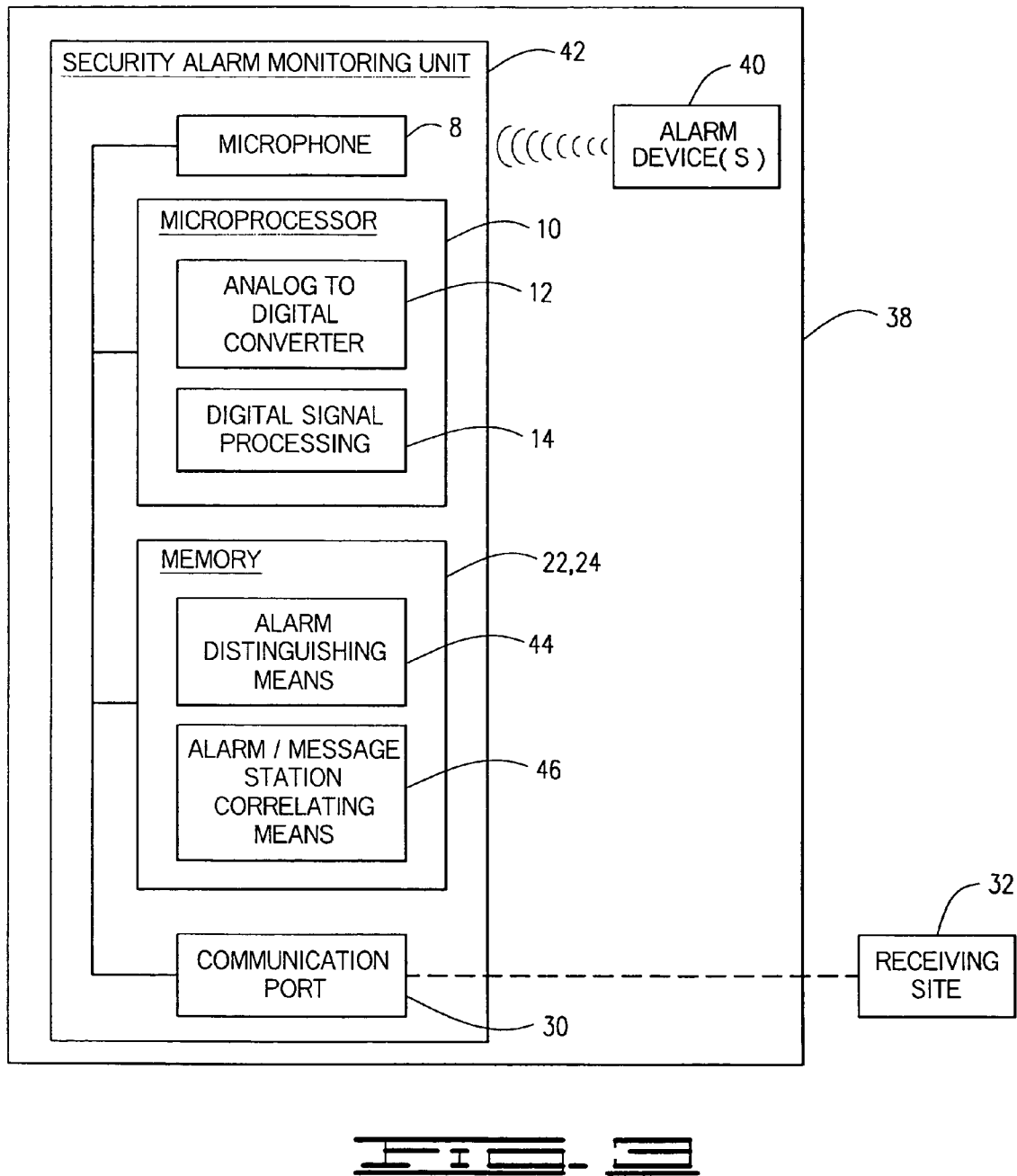
FIG. 3 is a block diagram of a home safety and security monitoring system of the present invention.

Referring to FIG. 3, a home safety and security system 38 of this invention includes a sound emitting security alarm device 40 and a security alarm monitoring unit 42, preferably a bedside unit. As with the fire alarm system, the bedside unit 42 "listens" for an alarm sound by combining the microphone 8 with microprocessor 10 comprising the analog to digital converter 12 and the digital signal processor 14. The microprocessor 10 utilizes the memory 22 which provides the storage substrate 24 for an alarm distinguishing means 44 and a means 46 for correlating the alarm with a specific message and receiving station. Upon detecting the security alarm 40, the microprocessor 10 generates the appropriate alarm message which is communicated through the communications port 30 to the appropriate receiving site 32.

Combining audio alert-producing security devices such as those available from e.g., RadioShack®, with the bedside fire alarm unit described above, provides a low-cost intrusion monitoring service. Thus the same security, and peace-of-mind benefits enjoyed by affluent homeowners will be brought to the "rest of the housing market." For example, glass-breaking detectors, readily available from ADEMCO (a unit of Honeywell Security Group), Database Systems Corp. (DSC) and others, may be placed on or near the lower windows of a home. Simple glass-break detectors react to the frequency of breaking glass while others use a filtered microphone to eliminate false alarms. They are widely available and reliable. Rather than hardwiring the glass-break detector to a complex home monitoring system, as is typically done, the detector activates an acoustic alarm which can be detected by the microphone and microprocessor in a bedside unit. The bedside unit will respond to the alarm by connecting to a standard phone system or to the Internet in a wired or wireless manner to send an alert or message to the local law enforcement agency or to a network operating center monitoring station. For example, the bedside unit may connect through an RJ-11 jack to a phone system to deliver the alert or message to a local police department.

In a preferred mode, a system provides both monitoring in response to an audible security alarm and waking mechanisms in response to a smoke alarm. For example, a bedside unit comprises a clock built to detect both a smoke alarm as well as a sound-producing motion detector from RadioShack®. The equipment is basically as previously described; however the fire alarm determining means 26 is modified to determine and distinguish more than one audible alarm sound pattern. Thus the alarm distinguishing means 44 identifies and distinguishes between the smoke alarm and the motion detector alarm and delivers separate responses. The previously described switch activating means 28 determines activation of the waking device in response to a smoke alarm. The alarm/message station correlating means 46 contains software to determine the alarm message and receiving site in response to the motion detector, and a separate alarm message and receiving site in response to the motion detector alarm. The response to the smoke alarm may include an audible alarm with verbal evacuation instructions as previously described. The response to the motion detector may include sounding a loud, audibly distinguishable alert at the bedside and sending a text message alert via Short Message Service to virtually any digital cellular phone in less than 15 seconds. (Short Message Service, commonly referred to as SMS, is a service for sending text messages to a wireless device, e.g., mobile phone, pager, Blackberry™, etc.)

Another home safety application of this invention is geared toward the ever-growing numbers of seniors who are trying to remain independent and whose families are dealing with and worrying about the safety and health of their aging relatives. From the familiar "I've fallen and can't get up!" to unobserved accidents and health emergencies at night, the opportunity to have a bedside alarm unit in connection with a personal alarm pendant will provide peace of mind to families and an extra level of safety and security to seniors. Personal emergency pendants and wrist bands are available from numerous companies which allow the wearer to simply press a button on the pendant to send a wireless emergency signal to a base station device which is connected via the phone system to a monitoring service. The pendant or wrist band of this invention emits an acoustic alarm detectable by the bedside unit. The bedside unit responds by connecting wirelessly to send an alert or message to local paramedics, a monitoring service and/or to family members and neighbors available to help. Alternatively, the bedside unit may connect through, for example, an RJ-11 jack to a phone system to deliver the alert or message.

The bedside unit of this invention also provides unobtrusive monitoring of sleep patterns in seniors so that adult children can be notified if unusual patterns occur. For example, if an elderly woman living alone gets up to go to the bathroom and falls, breaking her hip, the bedside unit notes her getting out of bed (cessation of monitored breathing or change of bed weight monitored by a load sensor) at, for example 2:30 a.m., and if she does not get back into bed in 30 to 45 minutes (noted by the reoccurrence of monitored breathing or bed weight) an alert would be sent to a monitoring service and a call would be placed to her children or caregivers. In a similar embodiment, if an elderly person living alone does not arise from bed within some time period of their average wake-up time, an alert is sent.

Additionally, the bedside unit can be used by working parents to check on whether their school children are safely home from school. A door-open detector with an acoustic signal is utilized such that when the child opens the door, an acoustic signal is sounded. A common type of door sensor uses a permanent magnet placed in the woodwork of the door, opposite the hinges. When the door is closed the magnet is very close to a magnetic switch and holds the switch closed. When the door is opened, the switch is no longer held closed by the magnet and an alarm is sounded. These sensors are commonly used to activate a chime when people enter. When the acoustic signal is sounded, the signal is picked up and recognized by the bedside unit which, in response, sends a wireless or wired telephone or e-mail message to the parent notifying the parent that the child has arrived home. Alternatively, any door-open detector with an acoustic signal can be utilized, as can any motion detector placed to sense a door or person crossing the door frame.

Health Monitor

Home health monitoring can help to reduce costs and improve care for people who suffer from chronic illnesses. It allows individuals to stay in the comfort of their homes, and gives those individuals the peace of mind and security of knowing that "someone is watching over them." For example, nighttime activity, various breathing parameters (breathing rate, snoring, coughing, etc.), and restlessness during sleep can all be monitored by the basic bedside unit of this invention having a microphone, a microprocessor for distinguishing the sounds received, and a wired or wireless connection to a monitoring station, preferably through the Internet, and/or means to awaken the individual monitored or alert a caretaker in the home or elsewhere. Such a unit can not only provide an emergency response, but can also provide for long-term evaluation and possibly early detection of worsening of a number of disease states including asthma, chronic bronchitis, emphysema, and obstructive sleep apnea. The addition of simple electro-acoustic transducers such as a consumer wireless heart monitor chest strap, bed load sensor, accelerometer, pulse sensor and pulse oximeter, along with the signal receiver in the bedside unit will provide unobtrusive collection of numerous additional physiologic parameters so that diseases such as congestive heart failure, atrial fibrillation and coronary artery disease can be monitored, allowing early intervention to prevent acute decompensation.

Figure 4:
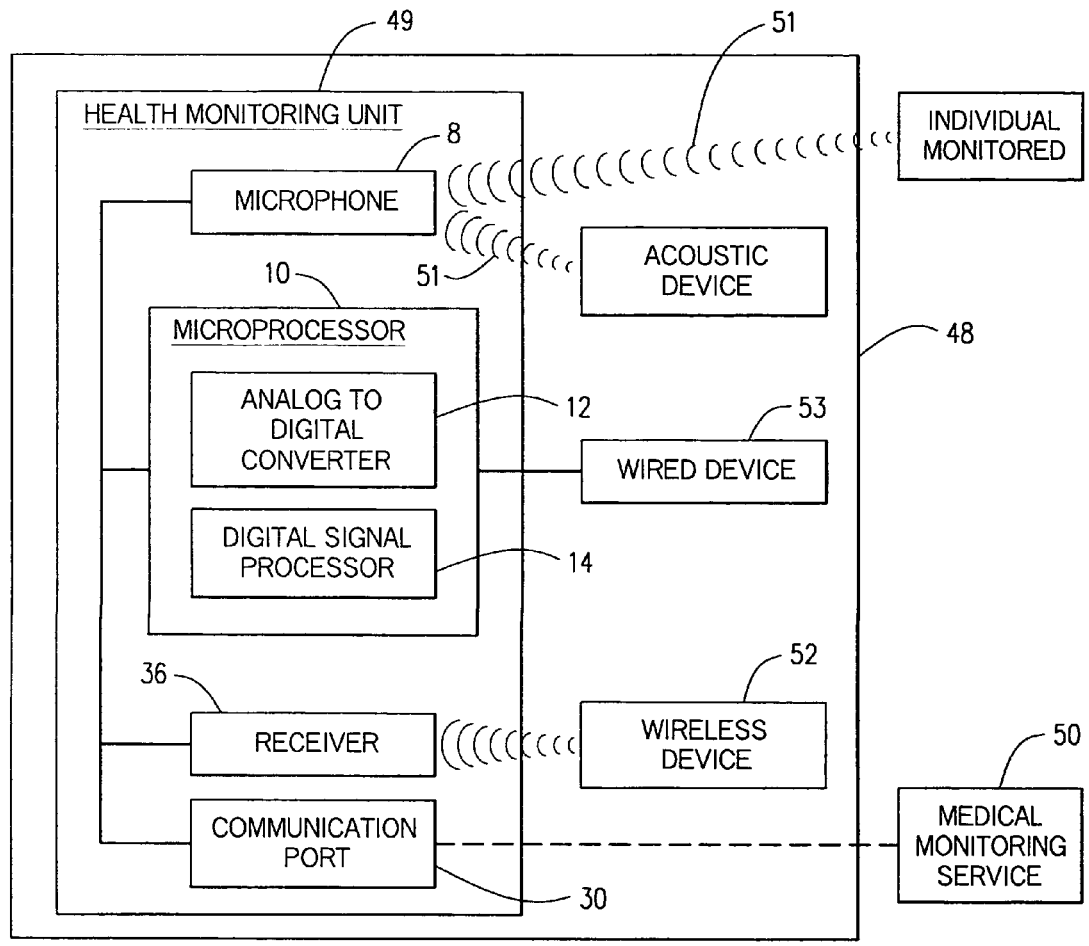
FIG. 4 is a block diagram of a home health monitoring system of the present invention.

Referring to FIG. 4, a home health monitoring system 48 of this invention includes a bedside health monitoring unit 49 having microphone 8 with the microprocessor 10 comprising the analog to digital converter 12 and optionally the digital signal processor 14. The microprocessor 10 passes signals derived from sounds detected by the microphone 8 through the communications port 30 to a medical monitoring service 50. The health related acoustic signals 51 are filtered using the digital signal processor 14 of the microprocessor 10 and/or the signals are filtered at the medical monitoring station. The present invention may utilize previously described digital signal analysis technology modified as necessary to identify one or more specific breathing pattern or acoustic signals from a medical monitoring device. Additionally, non-acoustic signals from one or more wireless 52, or wired 53, health parameter measuring devices are detected by the receiver 36 of the bedside unit 49 and relayed through the communications port 30 to the medical monitoring service 50.

Preferably, respiratory function and disease are evaluated via breathing rate (from either the microphone monitoring breathing sounds as acoustic signals 51 or a chest strap monitoring chest movement indicative of respiratory effort); the quantification of snoring, coughing, or apnea; and the frequency spectrum of the breathing sounds monitored (e.g., wheezing in asthma increases the frequency of the acoustic breathing sound pattern). Sleep is monitored with respiratory rate, heart rate, and activity (measured using the motion detector, load sensor or an accelerometer) in order to provide indices of sleep stage, restlessness and congestive heart failure status. When patterns portend a worsening of the condition, the appropriate health care professional and responsible people (e.g., parents, caretakers) are contacted by a medical monitoring group to allow for early intervention which will, hopefully, prevent serious outcomes, emergency room visits, and hospital admissions, if not tragic results.

Application of the bedside monitoring unit is described below for a number of common illnesses.

Asthma: This chronic respiratory disease is a major problem that is increasing in incidence in the pediatric population and is a major cause of hospitalization among children. However, children are not the only victims of this inflammatory airway disease. According to the American Lung Association, many millions of Americans suffer from asthma. It is a chronic inflammatory condition with acute exacerbations and can be a life-threatening disease if not properly managed.

Bedside monitoring at night is important because the disease often first manifests itself and can be evaluated by the presence of night coughing and snoring. Asthma attacks occur commonly at night, finally awakening the patient. Nighttime monitoring can warn a patient or parent of an upcoming attack before there are other symptoms. Early indications such as an increase in night coughing or snoring may alert an adult patient, parents or caregivers to worsening asthma and the need for immediate medication or other care.

An asthma monitoring system of this invention utilizes a bedside unit as previously described to monitor various breathing parameters including breathing rate, breathing sound frequency spectrum, snoring and coughing. The breathing parameter data are relayed to the medical monitoring service 50.

A method of this invention for providing a medical monitoring service for asthma comprises receiving at a medical monitoring service location, signals comprising breathing patterns wherein the breathing pattern signals are relayed out a communications port of a bedside home health monitoring unit, and analyzing the signals for changes to determine when the signals indicate a medical response is required. Examples of breathing patterns monitored and analyzed include, but are not limited to, breathing rate, breathing sound frequency spectrum, snoring and coughing. A spectral analysis of the breathing sounds monitored will provide an indication of wheezing. Asthma involves the constriction of airways, increasing the acoustic frequency of breathing sounds. The quantification of coughing, i.e., the number of coughs per unit time, provides an index of asthma severity and the effectiveness of medication.

Chronic Obstructive Pulmonary Disease: Clinically, Chronic Obstructive Pulmonary Disease (COPD) is a term that is used for two closely related diseases of the respiratory system: chronic bronchitis and emphysema. In chronic bronchitis, the trachea and bronchial tubes become irreversibly inflamed, restricting airflow, causing excessive mucous secretion leading to a persistent cough. In emphysema there is permanent destruction of the tiny elastic air sacs of the lung (called alveoli), which cause collapse or narrowing of the smallest air passages (called bronchioles), limiting airflow out of the lung. The walls of the alveoli are where the blood flow and airflow make their gas exchange. Without this exchange carbon dioxide builds up in the blood and blood oxygen diminishes.

As COPD progresses, the amount of oxygen in the blood decreases, causing blood vessels in the lung to constrict. At the same time many of the small blood vessels in the lung have been damaged or destroyed as a result of the disease. As a consequence, more work is required from the right ventricle of the heart to force blood through the narrowed vessels, causing the ventricle to enlarge and thicken (corpulmonale), and can lead to right-sided heart failure. Another adjustment the body makes to inadequate blood oxygen levels is called secondary polycythemia, which is an increased production of oxygen-carrying red blood cells. Over-population of red cells thickens the blood so much that it clogs small blood vessels, causing patients to have a bluish tinge to their skin, lips, and nail beds, a condition called cyanosis.

COPD gradually worsens over time. The main symptoms are coughing, wheezing, expectoration and labored breathing/shortness of breath. Exacerbations of COPD can happen several times per year and are sometimes brought on by respiratory infections, such as pneumonia and influenza. Home monitoring of night breathing can provide valuable data to guide bronchodilator, oxygen and other therapy.

A COPD monitoring system of this invention utilizes a bedside unit as previously described to monitor the same breathing patterns as the asthma monitoring system and to deliver the information to a medical monitoring service. A method of this invention for providing a medical monitoring service for COPD is basically the same as the medical monitoring service for asthma, modified in that the acoustic breathing pattern signature of decompensation in COPD is different than the signature indicating an oncoming asthma attack, and the medical reponses required are specific to each disease.

Cardiovascular Disease:

There are millions of new patients and tens of millions of existing patients with cardiovascular disease in the U.S. Out of the hospital monitoring has been limited to ambulatory electrocardiogram (Holter) monitoring and cardiac event recording. Now, companies such as CardioNet, Inc.; HomMed, LLC; Medtronic, Inc. and Guidant Corp. are creating innovative home cardiac monitoring solutions. All of these solutions involve expensive (and in some cases, implanted) equipment and services. This invention for monitoring cardiovascular disease allows for inexpensive and noninvasive methods and systems for home monitoring of physiologic variables predictive of cardiovascular disease progression or decompensation.

The basic health functions that monitor sleep and breathing can also be carried out on the previously described basic bedside unit used to monitor acoustic alarms. In addition, the use of a wireless chest strap, like those sold by Polar, Timex and others will provide a large number of additional physiological parameters to monitor. Preferably, a commercially available heart rate chest strap is modified to sense and transmit the following parameters during sleep over the one to four feet to the bedside unit using the existing short-range wireless communications in the strap: (a) beat-to-beat R-wave intervals; (b) QRS duration; (c) chest movement-respiratory effort; and (d) activity. The R-wave intervals and QRS duration are measured as an electrocardiogram (ECG) and transmitted using an existing chest strap described above.

Alternatively, ECG data can be detected using a hand held and operator actuated device 51 that then transmits the data as an acoustic signal to the microphone 8 of the bedside health monitoring unit. The Heart Card™ is one example of such a device and is commercially available from Instromedix, Inc. of Hillsboro, Oreg. Other devices are available from Instromedix, Inc. and other vendors to record the ECG as a frequency modulated audio band signal and these units can be adapted as necessary to yield acoustic signals detected by the microphone of the bedside unit of this invention.

Chest movement, which is indicative of respiratory effort, is measured using a strain gauge in the chest strap. Activity is measured using any commercially available accelerometer in the chest strap or in a sensor in the bed. Strain gauge and accelerometer measurements are transmitted to the bedside unit in the same manner as the wireless ECG measurements. Additionally, a patient's morning weight can be monitored by a load sensor in the bed. Thus, congestive heart failure patients, atrial fibrillation patients, and post-myocardial infarction patients can be monitored at home, allowing early interventions, improved outcomes and major cost savings.

Many studies have reported that resting heart rate is intimately related to the prognosis of cardiovascular disease. However, the heart rate in the waking state is influenced by psychological and physical activity and has low reproducibility. Therefore, heart rate should be measured throughout sleep with the non-REM values averaged as a time base heart rate. This invention provides for this measurement.

Also, studies have reported a circadian variation in the onset of acute myocardial infarction, or heart attack, with a peak occurrence in the number of heart attacks as the autonomic nervous system wakes up in the early morning. Atrial fibrillation is the most frequently encountered cardiac arrhythmia and a major risk factor for stroke and premature death.

Thus, in addition to alerting patients and caregivers of a possible oncoming heart attack, the bedside monitoring unit of this invention provides valuable long-term insight into the cardiac, respiratory, and weight status of patients suffering from cardiovascular disease. Preferably, the cardiovascular disease monitoring method, system and service of this invention monitors patients suffering from coronary artery disease and cardiac arrhythmia, especially atrial fibrillation. Also, the cardiovascular disease monitoring method, system and service of this invention monitors post-myocardial infarction patients, post-stroke patients, and congestive heart failure patients.

A method of this invention for providing a medical monitoring service for cardiovascular disease comprises receiving at a medical monitoring service location, signals comprising cardiovascular patterns wherein the cardiovascular pattern signals are relayed out a communications port of a bedside home health monitoring unit, and analyzing the signals for changes to determine when the signals indicate a medical response is required. Nonexclusive examples of cardiovascular patterns monitored include the breathing patterns described for asthma and COPD as well as beat-to-beat R-wave intervals, QRS duration, chest movement-respiratory effort, and activity. The combination of R-wave interval and QRS duration provides the fundamental information necessary for cardiac rhythm analysis thus providing for the detection of atrial fibrillation and conditions such as ventricular tachycardia.

Obstructive Sleep Apnea: Obstructive sleep apnea (OSA) or sleep disordered breathing (SDB) has garnered increasing attention as its relationship to other diseases has become better understood. Significant percentages of coronary artery disease patients, congestive heart failure patients, post-stroke patients and drug-resistant hypertensive patients have OSA/SDB. Recent studies have demonstrated that therapy for OSA improves congestive heart failure in patients with both problems. The only way to diagnose OSA/SBD has been in expensive sleep units in hospitals or attended in-home sleep studies. Most experts believe that this problem is significantly under-diagnosed and under-treated.

A sleep apnea monitoring system of this invention utilizes the same basic bedside unit as described for monitoring asthma. In a preferred embodiment, the system is modified to include the chest strap as described for monitoring cardiovascular disease.

A method of this invention for providing a medical monitoring service for sleep apnea is basically the same as the medical monitoring service for asthma, modified in that the acoustic breathing pattern changes indicating a medical response is needed are different for sleep apnea compared to asthma. Preferably the monitoring service also monitors signals from the chest strap for R-R interval and chest movement indicating respiratory effort.

Personal Computer Systems

Many residences in the U.S. and other countries have an Internet-connected personal computer. This number continues to grow, albeit at a slower rate than over the last ten years. The present invention provides a screen-saver or other program which can be purchased from a retail distributor or downloaded from a Web site. When the program activates, it will utilize the microphone and sound card that has been standard on all PCs since the mid 1990s to monitor for specific alarm sounds. In a preferred embodiment, the program detects the ISO/ANSI smoke detector audio signal; however, the program detects other audio alert-producing devices such as motion sensors, alert pendants, and door and window sensors, in addition to smoke detectors, by either learning new alarm sounds or drawing on a pre-existing library of alarm sounds. Upon detecting the audio alert, the program sends an e-mail or Internet instant message of the user's design to an address selected by the user. In another embodiment, the program detects health indicating parameters, preferably breathing-related sounds, and relays the parameters to a health monitoring service.

Figure 5:
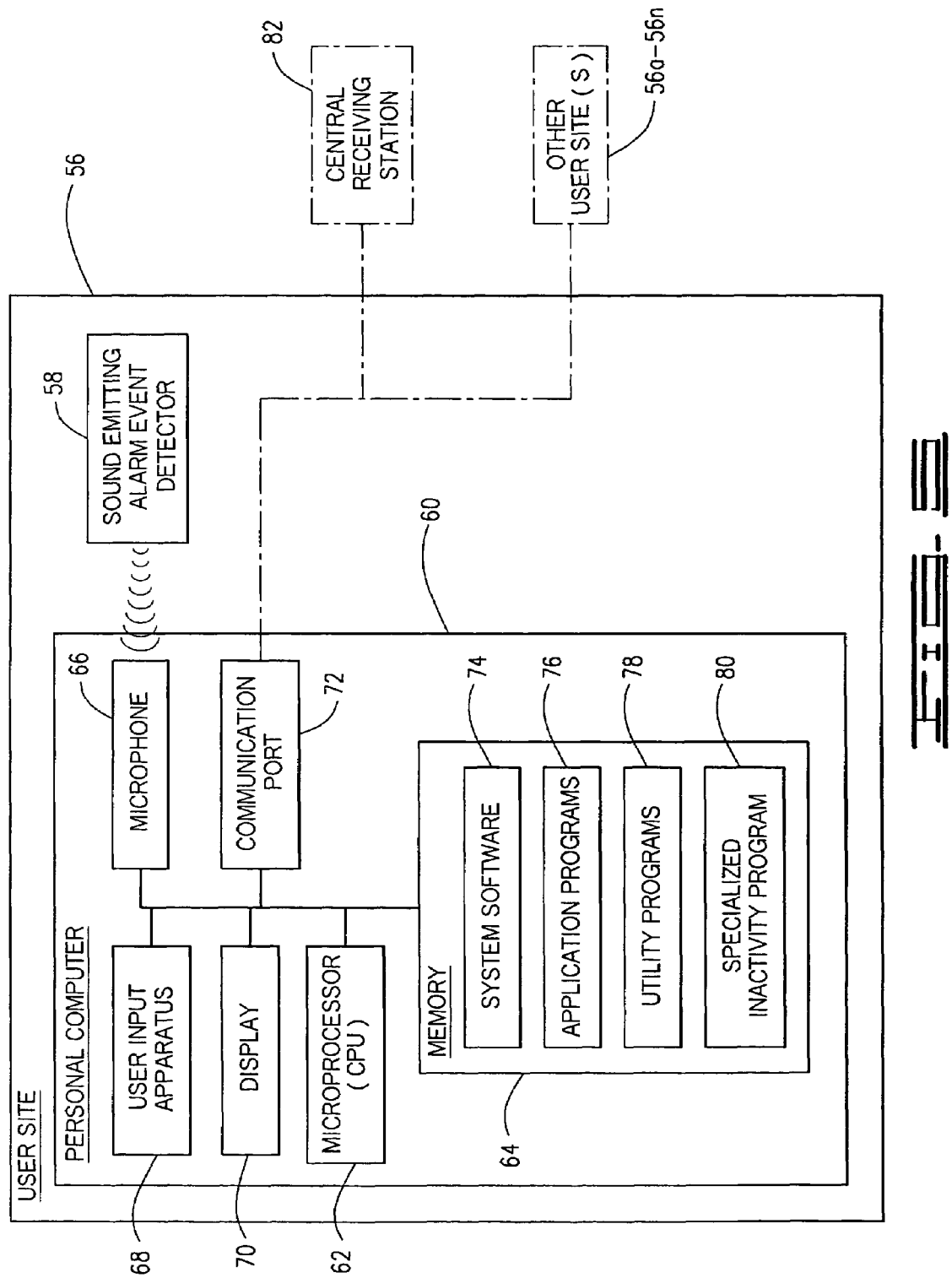
FIG. 5 is a block diagram of an alarm monitoring system using a personal computer.

An alarm monitoring system, including an alarm monitor and memory device, in accordance with the present invention is represented in FIG. 5. Such system can be used to implement the method of the present invention for monitoring for alarm sounds with a personal computer. This can also be used for implementing a method for providing for alarm monitoring in a residence in accordance with the present invention. Such system, monitor, and memory device may be used for other purposes, and the methods of the present invention can be implemented in other manners as well.

Referring to FIG. 5, a user site 56 includes a sound emitting alarm event detector 58 and a personal computer 60. The sound emitting alarm event detector 58 detects an alarm event and emits a sound having one or more identifiable characteristics or specifications. Examples of sound emitting alarm event detectors and alarms useful in the present invention include, but are not limited to, fire detector alarms, severe weather alarms, burglar or intruder detector alarms, carbon dioxide alarms and personal alarms as described in the preceding sections. Non-limiting examples of sound emitting fire detectors include residential smoke detectors and heat detectors. With regard to a smoke detector, for example, it is preferably one that provides a predetermined sound output such as in accordance with the National Fire Alarm Code three-pulse code known in the art. Non-limiting examples include smoke detectors providing single tone signals that are pulsed on and off, such as tones within the frequency range between 1 kilohertz and 4 kilohertz and with a pulse modulation rate between 3 and 8 hertz.

Non-limiting examples of severe weather alarms include sirens and emergency warning systems sounded by cities and other municipalities. These sirens can be quite effective when one is outside and near the sound source. However, sirens lose their effectiveness with distance and can become difficult to hear when the listener is inside a residence and possibly asleep.

Non-limiting examples of burglar or intruder detectors include a glass-breaking sensor, a door or window open sensor, and a motion sensor such as a passive infrared motion detector as previously described. As noted previously, the door-open sensor can also be activated by a child coming home from school rather than a burglar or intruder. In this case, the working parent can be notified that his/her child is home.

The present invention can also be implemented to respond to a personal alarm such as might be worn by an elderly person and activated when the person requires emergency assistance. For example, when such a person falls, cannot get up and cannot reach a phone, the person may sound an alarm using a device worn on the body or attached to the person's clothing. Such devices are available in retail stores such as RadioShack®.

The present invention can also be implemented to respond to other sound producers as well. Non-limiting examples include a doorbell, a telephone, a dog's bark, and a person's voice.

Of whatever type, the detector 58 or other sound source preferably provides an output sound having at least one identifiable or distinguishing characteristic so that the sound can be detected as defining the occurrence of an alarm event. If the alarm is a standard signal such as one specified by the National Fire Alarm Code, the choice of alarm to be monitored can be selected from a list of audible alarm options during setup of a specialized sound monitoring computer program. Alternatively, the alarm to be monitored can be activated by a personal computer user for setup purposes such that the sound is detected by the computer in a learning mode and identified as indicating an alarm event. The alarm sound to be monitored, whether selected or "learned," can be reset at any time and is not restricted to the sound selected during initial setup.

The present invention can also be implemented to monitor health indicating parameters of an individual. In this case, the specialized sound monitoring program is modified to identify health indicating parameters such as breathing rate, breathing sound frequency spectrum, snoring and coughing. The identified health indicating parameters are relayed through the communication port of the personal computer to a medical monitoring service.

Another device that can be included in the present invention is a repeater to relay sound. A non-limiting example is a conventional baby monitor positioned in a house to relay sound from a smoke detector (or other alarm-indicating sound source) to a microphone connected to the personal computer 60. Another example is a conventional baby monitor positioned near the bedside of an individual to relay breathing parameters to a microphone connected to a personal computer located in another part of the house.

The personal computer 60 of the present invention is preferably one provided with an integral or integrated microphone; however, other types of personal computers having microphones can also be used. More generally, "personal computer" as used in this description and in the claims encompasses any digital apparatus having a microprocessor and designed to be used by one person at a time. Preferably the personal computer uses a screen saver or other inactivity program, senses user activity and goes to an inactive state when there is no input activity during a predetermined time period. Non-limiting examples from existing technology include: palmtop, notebook, laptop and desktop computers; personal digital assistants; wireless communication equipment; and any other digitally intelligent apparatus in the home or workplace that can detect ambient sound and accept user programs. Preferably, the personal computer can access the Internet or other global communication network.

Referring to FIG. 5, preferable features of such apparatus include one or more of the following: microprocessor per se or other digitally implemented controller or central processing unit (cpu) 62, memory 64, microphone 66, user input apparatus 68, and one or more output devices such as a display 70 or a communications port 72. The cpu 62 is any suitable digital control apparatus capable of controlling or functioning within the operations described in this specification.

The memory 64 provides the storage substrate for program storage space and operational working space, and it can be implemented by one or more memory devices compatible with the selected cpu. Referring to FIG. 5, the storage space is used for storing system software 74 (e.g., Windows-brand or Apple-brand operating systems), application programs 76 (e.g., word processing programs), utility programs 78 (e.g., device drivers), and a sound monitoring program 80 of the present invention. The sound monitoring program 80 can be made to run in the background such that the personal computer is free to interact with the user and run other programs in the foreground. Preferably, the sound monitoring program 80 is a specialized inactivity program such that operation of the specialized inactivity program is initiated only during periods of computer user inactivity regarding the personal computer input and the specialized inactivity program includes a screen saver routine suitably defined for use in what can be otherwise conventional hardware and software of the personal computer.

The microphone 66 used in the personal computer 60 of the present invention connects to a conventional sound processing card providing analog to digital conversion by which the analog alarm-indicating sound waveform is converted into a digitized file stored in the memory 64 under control of the cpu 62. One example of this is a 16-bit signal acquisition card with selectable sampling frequency.

User input apparatus 68 of the personal computer can include, for example, a keyboard, a mouse, a light pen, a touch screen, or other suitable interface connected in known manner with the cpu 62.

The output device(s) are driven under control of the cpu 62 and they can include, for example, a conventional display, such as the monitor or other display screen 70, a speaker, or other device for providing external communication. The output device preferably also provides one or more communication ports 72 through which desirable communications can be made to, for example, the Internet or its World Wide Web, a pager system, a telephone system, or another e-mail system. Such communication can be via a wireless or hard-wired medium at any suitable bandwidth; however, a broadband communication is preferred.

One example of a preferred embodiment of the present invention includes a smoke detector alarm, a conventional desktop personal computer with microphone, a screen saver program of the present invention stored in memory of the personal computer, a broadband communication link from an output port of the personal computer, and a central receiving or monitoring station 82. Such central receiving station is illustrated in FIG. 4 and includes a computer having a plurality of sound monitoring screen saver programs stored in it. This can be a pre-existing or dedicated Internet site or other dedicated computer with which the local personal computer at the user site can communicate. Alarm notification messages e.g., smoke, intrusion or personal emergency, are received and acted upon by the dedicated computer automatically or by a human who is monitoring the dedicated computer either on site or remotely via a wired or wireless connection to the computer. For example, emergency personnel may be dispatched for certain alarm notification messages.

Because typically there is a plurality of user sites, FIG. 5 also illustrates other user sites 56a-56n that can be included in the system of the present invention. Each of the sites preferably includes at least one respective conventional personal computer having a microphone, system software and means for communicating with the computer at the central receiving station, such as to download from the computer at the central receiving station a respective one of the sound monitoring programs, preferably a background or a screen saver application, compatible with the system software in the respective personal computer or otherwise to communicate with the central receiving station. Each of these user sites further preferably includes at least one smoke detector (or other detectable sound producer) that emits a characteristic sound in response to detecting smoke (or providing other event notification) at the respective site. Such sound is detected by the microphone of the respective personal computer, but it is processed within the respective personal computer only in response to the respective downloaded (or otherwise previously loaded) sound monitoring program running in the foreground or background of the personal computer, and only during user inactivity periods if the sound monitoring program is a screen saver application. In such a network of computers, each station computer becomes a safety or security node that can generate its own signals as well as pass on signals it has received (either electronically or via its own speakers, for example).

Figure 6:
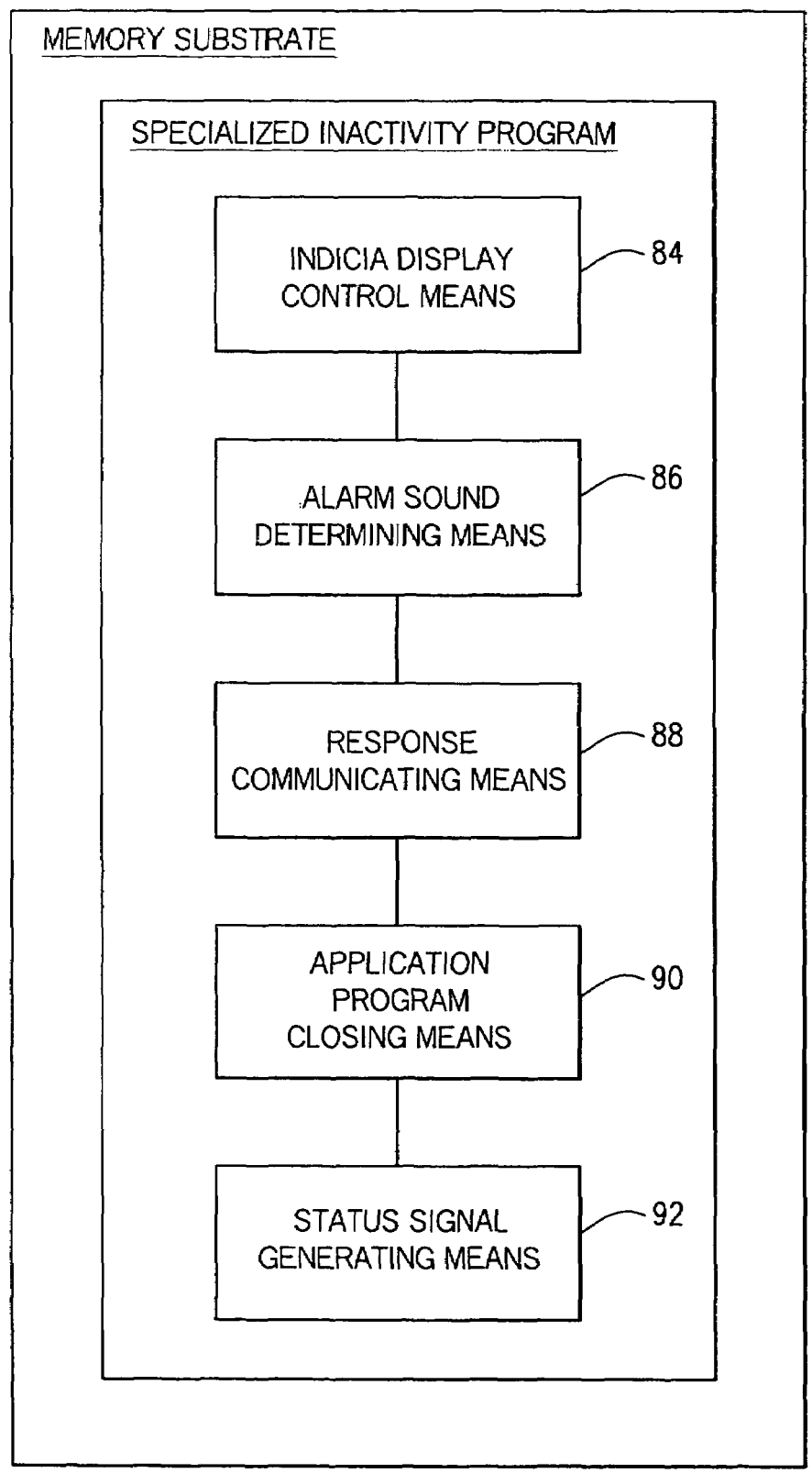
FIG. 6 is a block diagram representing a memory programmed in accordance with the present invention.

A sound monitoring program disposed on a memory substrate used in a personal computer in accordance with the present invention is illustrated in FIG. 6 as including indicia display control means 84, alarm sound determining means 86, response communicating means 88, application program closing means 90, and status signal generating means 92.

The indicia display control means 84 includes instructional signals encoded on the memory for cooperatively functioning with the system software of the personal computer to control what indicia are displayed on the display of the personal computer. For example, it may be desirable to indicate by a display when the sound monitoring program is running and functioning properly or when an alarm condition is detected. In a screen saver application of the sound monitoring program, the indicia display control means 84 includes instructional signals encoded on the memory for cooperatively functioning with the system software of the personal computer to control what indicia are displayed on the display of the personal computer during user inactivity periods. These first instructional signals can include signals defining advertising indicia to be displayed on the display of the personal computer. Such advertising can be used to pay for the costs of the programming or services of a business providing use of the present invention.

The alarm sound determining means 86 includes instructional signals encoded on the memory for cooperatively functioning with the system software to determine when sound received through the microphone of the personal computer is an alarm sound. Such signals can be implemented to provide intelligent signal processing, such as including stored or user-generated templates or a library of alarm templates defined by tables, or algorithms for processing the digitized sound signal received through the microphone of the personal computer. The acoustic signal recognition technology utilized is basically the same as described for the bedside unit, but modified as necessary for use in a personal computer.

The response communicating means 88 includes instructional signals encoded on the memory for cooperatively functioning with the system software to communicate responsive signals from the personal computer when an alarm sound is determined. Responsive signals are basically the same as those described for the bedside units.

The application program closing means 90 enables the response communicating means 88 to be dedicated to communicating responsive signals when an alarm sound is determined. To provide this, the sound monitoring program, and particularly the application program closing means of it, includes instructional signals encoded on the memory for cooperatively functioning with the system software to close application programs running on the personal computer at the time the sound monitoring program determines an alarm sound. This is particularly important in instances where the response communicating means is tied up with another application when an alarm sound is determined, for example, when the personal computer is already connected to an Internet site at the time a smoke detector alarm is determined.

The status signal generating means 92 includes instructional signals encoded on the memory substrate for cooperatively functioning with the system software to generate status signals to be transmitted to a remote location to indicate operational status of the personal computer when the sound monitoring program is in operation in the personal computer.

Further details of the foregoing will become apparent in the following explanation referring to FIGS. 7-10.

Figure 7:
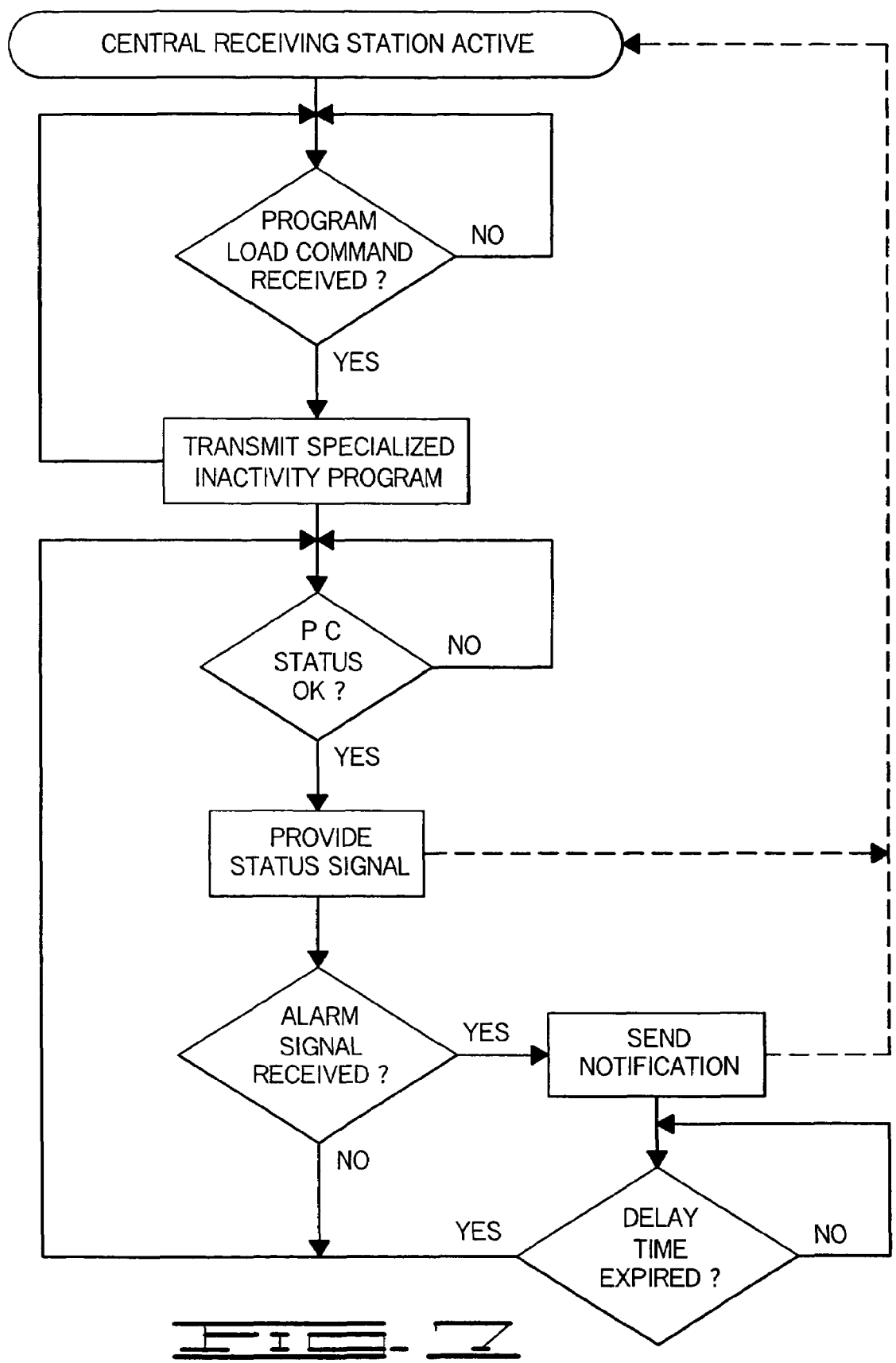
FIG. 7 is a flow diagram of programming for a central receiving station and a user's personal computer implementing the present invention.

Referring to FIG. 7, this represents communications between the central receiving station 82 when it is active and the personal computer 60 at one of the user sites. Initially, the personal computer 60 at the user site does not include a sound monitoring program in accordance with the present invention. Such program is, however, eventually loaded on the personal computer 60 by local or remote loading. To provide such program in one embodiment of the invention, the central receiving station 82 monitors communications to determine if it has received from the personal computer 60 a program load command, such as via the Internet to which both the control receiving station and the user site personal computer are connected in this example. If it has received a program load command, the central receiving station 82 transmits the specialized sound monitoring program compatible with the operating system of the respective personal computer. That is, in a particular implementation the sound monitoring program is downloaded from the Internet Web site into the personal computer having conventional hardware and system software with which the sound monitoring program is functionally compatible. If the sound monitoring program is a screen saver application, the sound monitoring screen saver program is downloaded from the Internet Web site into the personal computer and made the default operational program for each time the computer goes into its relevant user inactivity mode. Part of the program load command from the personal computer 60 can include credit card or other payment information by which a provider of the screen saver program or download service can receive payment.

The central receiving station 82 can also download other encoded signals. For example, it can transmit from the Internet site to the personal computer 60 digitally encoded advertising indicia signals such that the sound monitoring screen saver program automatically causes advertising indicia to be displayed through the display of the personal computer when the sound monitoring screen saver program is running. This can be an additional or alternative means for paying for use of the present invention.

The central receiving station 82 also monitors for status signals from the remote user sites 56, 56a-56n. The central receiving station can generate status inquiries or the remote sites can automatically contact the central station and send status signals, such as tones or "pings" to signify proper operation. As shown in FIG. 7, if the status of a respective personal computer is not okay, the personal computer loops to recheck its status or performs some remedial operation, such as a reboot if so programmed. If the status is okay, the status signal is provided to the central receiving station and the personal computer at the user site determines whether an alarm signal has been received. If not, the personal computer returns to check its status and repeats the foregoing. If an alarm signal has been received, notification is sent to the central receiving station and a delay (not shown) is implemented to prevent multiple notifications being sent for the same detected alarm event. As shown in FIG. 7, once the delay time has expired, the personal computer loops to recheck its status. The central receiving station monitors the Internet (if that is the communication link) to detect status signals sent from the personal computer to the Internet site of the central station, and it can be programmed to transmit a status notification from the central station Internet site when status signals are not received during a monitoring period. When the central receiving station receives an alarm indicating signal sent from the personal computer, the central receiving station can transmit a notification signal. The signals sent from the central station Internet site can be of any suitable type such as, without limitation, pager, telephone, or e-mail or other Internet transmissions. These communications can be directed to community authorities, such as the police or fire department, and they can be sent to the home owner/business owner (e.g., instant messages, e-mail, phone, cell phone "hotmail," 911, etc.).

Once a notification is sent from the user site, the respective personal computer 60 waits a predetermined delay time (e.g., thirty seconds) to avoid multiple notifications for the same event. The personal computer 60 then repeats the process as illustrated in FIG. 7. In the case of a false alarm, alarm transmission may be halted, for example, by entering a code on the keyboard. The indicia display control means 84 may cause a message to be displayed on the display 70 notifying users of the need for a key code entry if the alarm is false. This is useful in instances when an event such as cooking sets off the smoke alarm. Additionally, speakers attached to the personal computer may echo the alarm to enhance the audibility and notify users of the need for a key code entry if the alarm is false.

FIG. 8 shows a flow diagram for the process by which a respective personal computer 60, which has been turned on, initiates use of the sound monitoring screen saver program of the present invention that has been loaded in the personal computer. In a preferred embodiment, this program initiation occurs conventionally under control of the normal operating programs of the personal computer by which user inactivity is determined. For example, if a keyboard entry is not entered within a certain time period, the computer initiates the user inactivity program. When the sound monitoring program is a screen saver application, alarm or other sound monitoring does not occur except when the user inactivity program is running, and therefore only sporadic monitoring for such sounds occurs. That is, it is sporadic because monitoring occurs using the screen saver application only during user inactivity. Such inactivity period is distinguishable from other personal computer timer features that may shut down the monitor, disk drives or other components of the personal computer to minimize power consumption. The user inactivity period to which the preferred embodiment of the present invention pertains is that by which the display screen is simply blanked or otherwise placed under control of a screen saver program. Typically this is a time-out event occurring because an externally generated input is not received by the personal computer within a predetermined time period during operation of the personal computer (e.g., a user fails to press a keyboard key within a predetermined time period).

Referring to FIG. 9, once the inactivity program of the illustrated preferred embodiment is running, it controls the display image shown on the display of the personal computer, it may close running application programs if necessary to enable detection of and response to alarm conditions, it sends status signals if the personal computer is properly operating, it detects alarm conditions via sound picked up by the microphone connected to the personal computer, and it provides one or more responses. More detailed aspects of these are shown in the flow diagram of FIG. 10.

In a preferred embodiment, controlling the display image includes displaying advertising indicia on a display screen of the conventional hardware during such periods of computer user inactivity and in response to the operating of the initiated sound monitoring screen saver program. This includes using the running screen saver program for displaying advertising indicia on a display screen of the personal computer. The advertising indicia are encoded in the sound monitoring screen saver program.

Closing the running application programs includes using the sound monitoring program for controlling the closing of running application programs in the personal computer if necessary to enable detection of and response to alarm conditions. The sound monitoring program determines the need to close application programs but may default to settings that are specified by the user in a setup mode.

To send a status signal, the method of this preferred embodiment periodically generates and sends out the communications port of the personal computer status signals during periods when the sound monitoring program or the sound monitoring screen saver program is operating properly within the personal computer. In one implementation this includes generating and sending tone signals to the central receiving station to indicate proper functioning of the sound monitoring program and personal computer.

Figure 10:
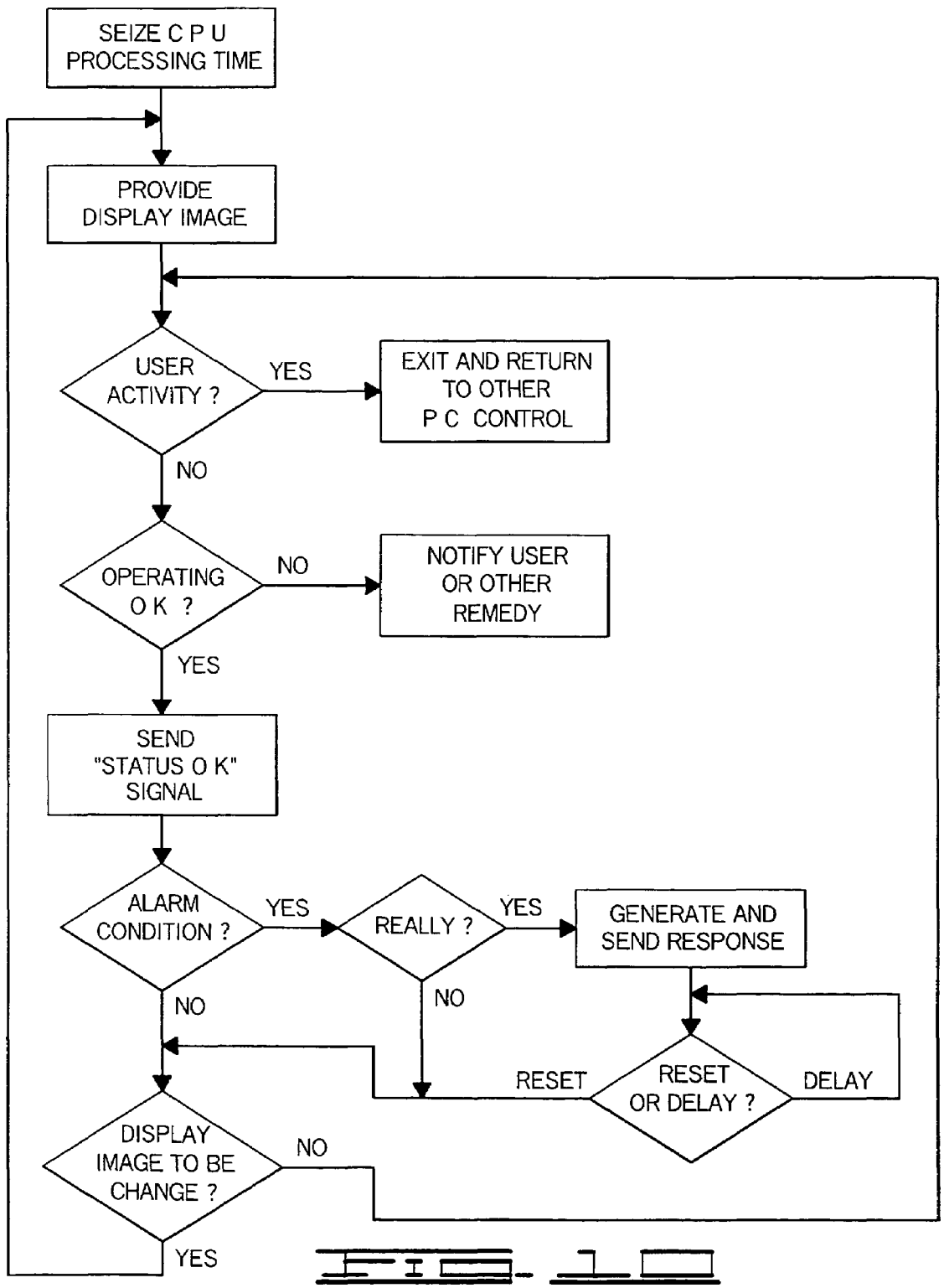
FIG. 10 is a more detailed flow diagram of a particular implementation of the programming of FIG. 9.

To detect an alarm condition, the microphone of the personal computer receives ambient sound. Alarm detection occurs under operation of the sound monitoring program in conjunction with at least portions of the conventional hardware and systems software in the personal computer 60. In a preferred embodiment, alarm detection occurs only during periods of computer user inactivity and under operation of the initiated sound monitoring screen saver program in conjunction with at least portions of the conventional hardware and systems software in the personal computer 60. Referring to FIG. 10, if an alarm condition is sensed, a delay or other analysis can be made to determine that it really is an actual alarm condition. If it is, a response is generated and sent, and then a subsequent delay is implemented to prevent multiple alarm signals being sent for the same alarm event. These delays can be for any suitable time, one non-limiting example of which is thirty seconds.

In detecting an alarm condition, the digitized file for the microphone-sensed sound waveform is compared in the personal computer to a predetermined template or other means for analyzing the detected sound and determining whether it represents an actual alarm event. This can include an algorithm that detects the presence of an alarm signal. A possible algorithm (1) transforms the sensed sound signal to the frequency domain by a series of Fast Fourier Transforms, (2) integrates and dumps the channels periodically to produce a spectrogram type array, and (3) examines the array to locate linear features that may be alarm signals. This can include rolling Fast Fourier Transforms (FFT) which enable the screen saver program to be trainable. Real-time detection algorithms applied to the digitized audio signals include frequency analysis (FFT), time-frequency analysis (running FFT), neural networks, correlation, matched filtering and other standard and advanced signal detection techniques. Such programs can learn what a specific alarm sounds like and form a template. This can also be used to adjust the sensitivity threshold for detection depending upon background audio noise level or other interference such as echos drowning the modulation of a standard smoke alarm.

When an alarm event is detected, the personal computer 60 provides a response. This is done using the running sound monitoring program. This includes generating and sending alarm indicating signals to the central receiving station 82, such as may be accessible via an Internet address encoded within the sound monitoring program. Such an alarm signal and automatic sending are preferably not contrary to any authorized automatic dialing technique. Many municipalities do not allow unlicensed auto-dial type equipment to call directly to police or fire service phones; thus, in such case the computer generated calls would need to be routed to a licensed alarm monitoring service company, which could in turn properly handle further notification to the authorities or to individuals, such as homeowners or business owners responsible for the locations where the user site personal computers are located.

The present invention can also be provided with an override feature whereby the alarm monitoring or the sending of an alarm signal can be halted if the personal computer is suitably actuated, such as by entering a key code via the keyboard within a certain time of the alarm detection.

Local responses can also be provided, such as by audible signals transmitted through the personal computer's speaker(s) under suitable volume control.

In still another preferred embodiment, a personal computer, preferably a Pocket PC Phone product, combines the sound monitoring program or screen saver of this invention with the dedicated alerting, wakeup and monitoring bedside unit described previously. This product provides for portable, wireless monitoring of smoke detectors and other audio alert-producing devices. This type of product can provide monitoring in portable or temporary buildings where wired phone line access is not available. Also, it can have both AC and 24 hours of battery backup power so that it meets the NFPA National Fire Alarm Code for fire monitoring systems. The product optionally utilizes a Global System for Mobile Communications (GSM) world phone wireless capability so it could be sold world-wide, and can include a Global Positioning System (GPS) receiver so that the wireless alerts can also provide the location of the product to fire or emergency personnel. The GPS aspect can also be used to identify where a given asset is located for insurance or lending collateral verification purposes.

Another embodiment of the present invention combines a personal computer, preferably a Pocket PC or Smart Phone product having the sound monitoring program of this invention, with a personal alert pendant and a GPS receiver. Such a system provides emergency alerts that include the location of the individual requiring assistance. While the personal alert is generally activated by an individual requiring immediate assistance, the system can also be adapted to be activated by a "break-in" of an automobile, thus providing notice of an attempted theft as well as the location of the car involved in the theft.

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by the appended claims.

What is claimed is:

1. An alarm monitor, comprising:
    a conventional personal computer including a microphone, a memory, a communication port, a display and system software; and
    a sound monitoring screen saver program stored in the memory, including:
        first instructional signals encoded on the memory for cooperatively functioning with the system software to determine when sound received through the microphone of the personal computer is an alarm sound; and
        second instructional signals encoded on the memory for cooperatively functioning with the system software to communicate responsive signals from the personal computer when an alarm sound is determined.

2. An alarm monitor as defined in claim 1, wherein the sound monitoring screen saver program further comprises third instructional signals encoded on the memory for cooperatively functioning with the system software to control what indicia are displayed on the display of the personal computer during input inactivity periods.

3. An alarm monitor as defined in claim 1, wherein the sound monitoring screen saver program additionally includes instructions for closing or overriding other running application programs in the personal computer when an alarm sound is determined.

4. An alarm monitor as defined in claim 1, wherein the sound monitoring screen saver program includes additional instructional signals encoded on the memory for cooperatively functioning with the system software to generate status signals to be transmitted to a remote location to indicate operational status of the personal computer when the alarm sound monitoring program is in operation rn the personal computer.

5. An alarm monitor as defined in claim 1, further comprising a Global Positioning System receiver for cooperatively functioning with the system software and the sound monitoring screen saver program to determine location of the monitor when an alarm sound is determined, and wherein the responsive signals include said location.

6. An alarm monitor as defined in claim 1, wherein the personal computer is selected from the group consisting of desk top computers, lap top computers, notebook computers, handheld personal computers, palm tops, pocket computers, personal digital assistants and smart phones.

7. An alarm monitor as defined in claim 1, wherein the sound monitoring screen saver program is adapted to be initiated by a period of computer user inactivity regarding input to the personal computer.

8. An alarm monitor as defined in claim 1, wherein the first instructional signals include a digital acoustic signature recognition technology comprising a technique selected from the group consisting of matched filtering, cross correlation, and neural networking.

9. An alarm monitor as defined in claim 1, wherein the sound monitoring screen saver program is the default screen saver program in the personal computer.

10. An alarm monitor as defined in claim 1, wherein the sound monitoring screen saver program includes a library of acoustic alarm signals.

11. An alarm monitor as defined in claim 1, wherein the sound monitoring screen saver program includes instructions to provide, during initial setup, a list from which one or more standardized alarm sounds can be selected.

12. An alarm monitor as defined in claim 1, wherein the sound monitoring screen saver program includes a learning mode during initial setup allowing the alarm sound to be activated, detected and identified as such.

13. An alarm monitor as defined in claim 1, wherein the sound monitoring screen saver program includes instructions to download a library of acoustic alarm signals from an Internet Web site.

14. An alarm monitor as defined in claim 1, wherein the sound monitoring screen saver program is downloadable into the personal computer from an Internet Web site.

15. An alarm monitor as defined in claim 1, wherein the second instructional signals for communicating responsive signals include instructions for sending an alarm notification signal to an Internet Web site address encoded within the sound monitoring program.

16. An alarm monitor as defined in claim 1, wherein the sound monitoring screen saver program is downloadable into the personal computer from an Internet Web site, and wherein the second instructional signals for communicating responsive signals includes instructions for sending an alarm notification signal to the Internet Web site address.

17. An alarm monitor as defined in claim 1, wherein the second instructional signals for communicating responsive signals include instructions for sending an alarm notification signal to an Internet Web site address utilizing Internet instant messaging as a communications means thereby allowing the Internet site to monitor the online status of the sound monitoring program.

18. An alarm monitor as defined in claim 1, wherein the second instructional signals for communicating responsive signals include instructions for communicating to a telecommunication number or e-mail address.

19. An alarm monitor as defined in claim 1, wherein the second instructional signals for communicating responsive signals include instructions for sending an alarm notification signal to an Internet Web site address, and instructions for the Internet Web site to communicate to a telecommunication number or e-mail address designated for the personal computer.

20. An alarm monitor, comprising:
a conventional personal computer including a microphone, a memory, a communication port, a display and system software; and
a sound monitoring program stored in the memory, including:
  first instructional signals encoded on the memory for cooperatively functioning with the system software to determine when sound received through the microphone of the personal computer is an alarm sound, the first instructional signals including a digital acoustic signature recognition technology comprising a technique selected from the group consisting of matched filtering, cross correlation, and neural networking; and
  second instructional signals encoded on the memory for cooperatively functioning with the system software to communicate responsive signals from the personal computer when an alarm sound is determined.

* * * * *

UNITED STATES PATENT AND TRADEMARK OFFICE
CERTIFICATE OF CORRECTION

PATENT NO. : 7,403,110 B2
APPLICATION NO. : 11/494074
DATED : July 22, 2008
INVENTOR(S) : David E. Albert and Kathryn Marie Albert Page 1 of 1

It is certified that error appears in the above-identified patent and that said Letters Patent is hereby corrected as shown below:

In the Claims:

Column 28, line 14: After "operation" delete "m" and replace with -- in --.

Signed and Sealed this
Fifteenth Day of March, 2011

David J. Kappos
*Director of the United States Patent and Trademark Office*